(12) United States Patent
Pier et al.

(10) Patent No.: US 7,252,828 B2
(45) Date of Patent: Aug. 7, 2007

(54) **POLYSACCHARIDE VACCINE FOR *STAPHYLOCOCCAL* INFECTIONS**

(75) Inventors: Gerald B. Pier, Brookline, MA (US); Julia Y. Wang, Chestnut Hill, MA (US); David McKenney, Quincy, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/771,003

(22) Filed: Jan. 26, 2001

(65) Prior Publication Data

US 2002/0119166 A1 Aug. 29, 2002

Related U.S. Application Data

(63) Continuation-in-part of application No. 09/399,904, filed on Sep. 21, 1999, now abandoned, which is a continuation-in-part of application No. 09/354,408, filed on Jul. 15, 1999, now abandoned.

(60) Provisional application No. 60/093,117, filed on Jul. 15, 1998.

(51) Int. Cl.
| | |
|---|---|
| *A61K 39/02* | (2006.01) |
| *A61K 39/09* | (2006.01) |
| *A61K 39/00* | (2006.01) |
| *A61K 31/70* | (2006.01) |
| *C07H 1/00* | (2006.01) |
| *C07H 1/06* | (2006.01) |
| *A01N 43/04* | (2006.01) |

(52) U.S. Cl. ............... 424/234.1; 424/237.1; 424/184.1; 424/831; 536/123.1; 536/127; 514/23; 514/54; 514/62

(58) Field of Classification Search ............ 536/123.1, 536/127, 2–21; 514/23, 54, 62; 424/184.1, 424/234.1, 237.1, 831
See application file for complete search history.

(56) References Cited

U.S. PATENT DOCUMENTS

| | | | |
|---|---|---|---|
| 4,197,290 A | 4/1980 | Yoshida | 424/92 |
| 4,285,936 A | 8/1981 | Pier et al. | 424/180 |
| 4,443,549 A | 4/1984 | Sadowski | 436/548 |
| 4,578,458 A | 3/1986 | Pier | 536/123 |
| 4,652,448 A | 3/1987 | Sadowski | 424/87 |
| 4,786,592 A | 11/1988 | Deal et al. | 435/7 |
| 4,789,735 A | 12/1988 | Frank et al. | 530/395 |
| 4,795,803 A | 1/1989 | Lindberg et al. | 530/324 |
| 4,830,852 A | 5/1989 | Marburg et al. | 424/85.8 |
| 4,859,449 A | 8/1989 | Mattes | 424/9 |
| 4,879,272 A | 11/1989 | Shimoda et al. | 514/8 |
| 4,902,616 A | 2/1990 | Fournier et al. | 435/101 |
| 5,055,455 A | 10/1991 | Pier et al. | 514/54 |
| 5,362,754 A | 11/1994 | Raad et al. | 514/566 |
| 5,366,505 A | 11/1994 | Farber | 623/11 |
| 5,571,511 A * | 11/1996 | Fischer | 424/165.1 |
| 5,589,591 A * | 12/1996 | Lewis | 536/128 |
| 5,688,516 A | 11/1997 | Raad et al. | 424/409 |
| 5,718,694 A | 2/1998 | Rupp | 604/265 |
| 5,830,539 A | 11/1998 | Yan et al. | 427/551 |
| 5,858,350 A * | 1/1999 | Vournakis et al. | 424/93.1 |
| 5,866,140 A | 2/1999 | Fattom et al. | 424/243.1 |
| 5,980,910 A | 11/1999 | Pier | 424/266.1 |
| 5,989,542 A * | 11/1999 | Pier et al. | 424/93.48 |
| 6,245,735 B1 | 6/2001 | Pier | |
| 6,399,066 B1 * | 6/2002 | Pier | 424/165.1 |
| 6,743,431 B2 | 6/2004 | Pier | |
| 2002/0119166 A1 | 8/2002 | Pier et al. | |
| 2003/0124631 A1 | 7/2003 | Pier et al. | |
| 2004/0091494 A1 | 5/2004 | Pier et al. | |
| 2004/0175731 A1 | 9/2004 | Pier et al. | |
| 2005/0025775 A1 | 2/2005 | Pier et al. | |

FOREIGN PATENT DOCUMENTS

| | | |
|---|---|---|
| EP | 0 302 781 B1 | 2/1989 |
| EP | 0 694 309 A2 | 1/1996 |
| FR | 2 410 043 A1 | 6/1979 |
| FR | 2 581 877 A1 | 11/1986 |
| FR | 2640628 | 12/1988 |
| GB | 2 009 771 A1 | 6/1979 |
| WO | WO 85/05037 A1 | 11/1985 |
| WO | WO 86/02358 A1 | 4/1986 |
| WO | WO 88/02028 A1 | 3/1988 |
| WO | WO 89/04873 A1 | 6/1989 |
| WO | WO 90/03398 | 4/1990 |
| WO | WO 90/06696 A2 | 6/1990 |
| WO | WO 93/01276 A1 | 1/1993 |
| WO | WO 93/09811 A1 | 5/1993 |
| WO | WO 93/19373 A1 | 9/1993 |
| WO | WO 94/15640 A1 | 7/1994 |
| WO | WO 98/52605 A1 | 11/1998 |
| WO | WO 00/03745 A2 | 1/2000 |
| WO | WO 00/35504 A1 | 6/2000 |
| WO | WO 03/053462 A2 | 7/2003 |
| WO | WO 2004/043405 A2 | 5/2004 |
| WO | WO 2004/043407 A2 | 5/2004 |

OTHER PUBLICATIONS

Chu et al. Infect. Immun. 59: 4450-4458, 1991.*

(Continued)

*Primary Examiner*—S. Devi
(74) *Attorney, Agent, or Firm*—Wolf, Greenfield & Sacks, P.C.

(57) ABSTRACT

The invention relates to compositions of the capsular polysaccharide/adhesin (PS/A) of *staphylococci*. The PS/A may be isolated or synthesized and includes various modifications to the structure of native PS/A based on the chemical characterization of PS/A. The invention also relates to the use of the PS/A as a vaccine for inducing active immunity to infections caused by *Staphylococcus aureus, S. epidermidis*, other related coagulase-negative *staphylococci* and organisms carrying the ica (intracellular adhesin) locus, and to the use of antibodies directed to PS/A for inducing passive immunity to the same class of infections.

11 Claims, 6 Drawing Sheets

OTHER PUBLICATIONS

Baldassarri et al. Infect. Immun. 64: 3410-3415, Aug. 1996.*
Heilmann et al. Mol. Microbiol. 20: 1083-1091, Jun. 1996.*
Ammendolia, M.G. et al., "Slime Production and Expression of the Slime-Associated Antigen by Staphylococcal Clinical Isolates", *Journal of Clinical Microbiology*, Oct. 1999, pp. 3235-3238, vol. 37, No. 10, American Society for Microbiology.
Barsham, S. et al., "Detection of antibodies to *Staphylococcus epidermidis* in infected total hip replacement by an enzyme linked immunosorbent assay", *J. Chin. Patho.* 1985, pp. 839-840, vol. 38, No. 7.
Bernstein, J.M. et al., "Antibody coated bacteria in otitis media with effusions", *Ann. Otol. Rhinol. Laryngol. Suppl.* (United States), May-Jun. 1980, pp. 104-109 Abstract, vol. 89.
Capek, K. et al., "Liquid Column Chromatography: A Survey of Modern Techniques and Applications", *Journal of Chromatography Library Chapters 22-23*, 1975, pp. 465-528, vol. 3, Elsevier Scientific Publishing Company.
Chanter, N., "Partial Purification and Characterization of Two Non K99 Mannose-resistant Haemagglutinins of *Escherichia coli* B41", *Journal of General Microbiology*, 1983, pp. 235-243, vol. 129.
Chen, H. et al., "Characterization and Biological Properties of Chemically Deglycosylated Human Chorionic Gonadotropin-Role of Carbohydrate Moieties in Adenylate Cyclase Activation", *The Journal of Biological Chemistry*, Dec. 10, 1982, pp. 14446-14452, vol. 257, No. 23.
Christensen, G.D. et al., "Adherence of Slime-Producing Strains of *Staphylococcus epidermidis* to Smooth Surfaces", *Infection and Immunity*, Jul. 1982, pp. 318-326, vol. 37, No. 1.
Cramton, S.E. et al., "The Intercellular Adhesion (*ica*) Locus is Present in *Staphylococcus aureus* and is Required for Biofilm Formation", *Infection and Immunity*, Oct. 1999, pp. 5427-5433, vol. 67, No. 10, American Society for Microbiology.
Dobrin, R.S. et al., "The role of complement, immunoglobulin and bacterial antigen in coagulase-negative staphylococcal shunt nephritis", *Am. J. Med.* (United States), Nov. 1975, pp. 660-673 Abstract, vol. 59. No. 5.
Elder, B.L. et al., "Characterization of Monoclonal Antibodies Specific for Adhesion: Isolation of an Adhesin of *Streptococcus sanguis* FW213", *Infection and Immunity*, Nov. 1986, pp. 421-427, vol. 54, No. 2, American Society for Microbiology.
Espersen, F. et al., "Enzyme-linked immunosorbent assay for detection of *Staphylococcus epidermidis* antibody in experimental *S. epidermidis* endocarditis", *J. Clin. Microbiol.*, Feb. 1986, pp. 339-342 Abstract, vol. 23, No. 2.
Espersen, F. et al., "Solid-phase radioimmunoassay for IgG antibodies to *Staphylococcus epidermidis*. Use in serious coagulase-negative staphylococcal infections", *Arch. Intern. Med.*, Apr. 1987, pp. 689-693 Abstract, vol. 147, No. 4.
Fattom, A. et al., "Synthesis and Immunologic Properties in Mice of Vaccines Composed of *Staphylococcus aureus* Type 5 and Type 8 Capsular Polysaccharides Conjugated to *Pseudomonas aeruginose* Exotoxin A", *Infection and Immunity*, Jul. 1990, pp. 2367-2374, vol. 58, No. 7, American Society for Microbiology.
Ferreiros, C.M. et al., "Purification and Partial Characterization of a K99-Antigen Associated Adhesin in *Escherichia coli* (637 Strain)", *Revista Esparola De Fisiologia*, 1983, pp. 45-50, vol. 39.
Gerke, C. et al., "Characterization of the N-Acetylglucosaminyltransferase Activity Involved in the Biosynthesis of the *Staphylococcus epidermidis* Polysaccharide Intercellular Adhesin", *J. Biol. Chem.*, Jul. 17, 1998, pp. 18586-18593, vol. 273, No. 29.
Gray, E.D. et al., "Effect of Extracellular Slime Substance from *Staphylococcus epidermidis* on the Human Cellular Immune Response", *The Lancet*, Feb. 18, 1984, pp. 365-367.
Heilmann, C. et al., "Molecular basis for intercellular adhesion in the biofilm-forming *Staphylococcus epidermidis*", *Molecular Microbiology*, 1996, pp. 1083-1091, vol. 20, No. 5, Blackwell Science Ltd.
Hogt, A.H. et al., "Cell Surve Characteristics of Coagulase-Negative Staphylococci and Their Adherence to Fluorinated Poly(Ethylenepropylene)", *Infection and Immunity*, Jan. 1986, pp. 294-301, vol. 51, No. 1, American Society for Microbiology.
Johnson, G.M. et al., "Interference with Granulocyte Function by *Staphylococcus epidermidis* Slime", *Infection and Immunity*, Oct. 1986, pp. 13-20, vol. 54, No. 1, American Society for Microbiology.
Keutmann, H.T. et al., "Evidence for a conformational change in deglycosylated glycoprotein hormones", *FEBS 2637*, Jun. 1985, pp. 333-338, vol. 185, No. 2, Federation of European Biochemical Societies.
Lee, J.C. et al., "Protective Efficacy of Antibodies to the *Staphylococcus aureus* Type 5 Capsular Polysaccharide in a Modified Model of Endocarditis in Rats", *Infection and Immunity*, Oct. 1997, pp. 4146-4151, vol. 65, No. 10, American Society for Microbiology.
Leith, D.K. et al., "Purification of a *Mycoplasma pneumoniae* Adhesin by Monoclonal Antibody Affinity Chromatogrphy", *Journal of Bacteriology*, Feb. 1984, pp. 678-680, vol. 157, No. 2, American Society for Microbiology.
Locksley, R.M., "Chapter 94: Part 3 Disorders Caused by Biologic and Environmental Agents: Staphylococcal Infections", *Harrison's Principles of Internal Medicine, 11th Edition*, 1950, pp. 537-543.
Ludwicka, A. et al., "Investigation on Extracellular Slime Substance Produced by *Staphylococcus epidermidis*", *Zbl Bakt Hyg A*, 1984, pp. 256-267, vol. 258.
Mack, D. et al., "The Intercellular Adhesin Involved in Biofilm Accumulation of *Staphylococcus epidermidis* is a Linear $\beta$-1,6-Linked Glucosaminoglycan: Purification and Structural Analysis", *J. of Bacteriology*, Jan. 1996, pp. 175-183, vol. 178, No. 1, American Society for Microbiology.
Mack, D. et al., "Essential Functional role of the Polysaccharide Intercellular Adhesin of *Staphylococcus epidermidis* in Hemagglutination", *Infection and Immunity*, Feb. 1999, pp. 1004-1008, vol. 67, No. 2, American Society for Microbiology.
Mack, D. et al., "Identification of Three Essential Regulatory Gene Loci Governing Expression of *Staphylococcus epidermidis* Polysaccharide Intercellular Adhesin and Biofilm Formation", *Infection and Immunity*, Jul. 2000, pp. 3799-3807, vol. 68, No. 7, American Society for Microbiology.
McKenney, D. et al., "The *ics* locus of *Staphylococcus epidermidis* encodes production of the capsular polysaccharide/adhesin", *Infect. Immun.*, Oct. 1998, pp. 4711-4720 Abstract, vol. 66, No. 10.
McKenney, D. et al., "Broadly Protective Vaccine for *Staphylococcus aureus* Based on an *in Vivo*—Expressed Antigen", *Science*, May 28, 1999, pp. 1523-1527, vol. 284.
McKenney, D. et al., "Vaccine potential of poly-1-6 $\beta$-D-N-succinylglucosamine, an immunoprotective surface polysaccharide of *Staphylococcus aureus* and *Staphylococcus epidermidis*", *Journal of Biotechnology*, 2000, pp. 37-44, vol. 83, Elsevier Science B.V.
Moch, T. et al., "Isolation and characterization of the $\alpha$-sialyl-$\beta$-2,3-galactosyl-specific adhesin from fimbriated *Escherichia coli*", *Proc. Natl. Acad. Sci. USA*, May 1987, pp. 3462-3466, vol. 84.
Muller, E. et al., "Occurrence of Capsular Polysaccharide/Adhesin among Clinical Isolates of Coagulase-Negative Staphylococci", *The Journal of Infectious Diseases*, 1993, pp. 1211-1218, vol. 168, The University of Chicago.
Nagy, L.K. et al., "Multi-Adhesin Vaccines for the Protection of the Neonatal Piglet Against *E. coli* Infections", *Develop. Biol. Standard*, 1983, pp. 189-197, vol. 53, International Symposium on Enteric Infections in Man and Animals: Standardization of Immunological Procedures, Dublin, Ireland 1982.
Nakano, M. et al., "Polyclonal antibody production in murine spleen cells induced by Staphylococcus", *Microbiol. Immunol.* (Japan), 1980, pp. 981-984 Abstract, vol. 24, No. 10.
Orskov. I. et al, "An Adhesive Protein Capsule of *Escherichia coli*", *Infection and Immunity*, Jan. 1985, pp. 191-200, vol. 47, No. 1, American Society for Microbiology.
Peters, G. et al., "Biology of *S. epidermidis* Extracellular Slime", *Zbl. Bakt. Suppl. 16*, Gustav Fischer Verlag, Stuttgart, New York, 1987, pp. 15-33.
Pier, G.B. et al., "Isolation and Characterization of a High-Molecular-Weight Polysaccharide from the Slime of *Pseudomonas aeruginosa*", *Infection and Immunity*, Dec. 1978, pp. 908-918, vol. 22, No. 3, American Society for Microbiology.

Pier, G.B. et al., "Protective Immunity Induced in Mice by Immunization of High-Molecular-Weight Polysaccharide from *Pseudomonas aeruginosa*", *Infection and Immunity*, Dec. 1978, pp. 919-925, vol. 22, No. 3, American Society for Microbiology.

Pier, G.B. et al., "Further Purification and Characterization of High-Molecular-Weight Polysaccharide from *Pseudomonas aeruginose*", *Infection and Immunity*, Dec. 1983, pp. 936-941, vol. 42, No. 3, American Society for Microbiology.

Quie, P.G. et al., "Perspective: Coagulase-Negative Staphylococcal Adherence and Persistence", *The Journal of Infectious Diseases*, Oct. 1987, pp. 543-547, vol. 156, No. 4, The University of Chicago.

Rogemond, V. et al., "Lectinlike Adhesins in the *Bacteroides fragilis* Group", *Infection and Immunity*, Jul. 1986, pp. 99-102, vol. 53, No. 1, American Society for Microbiology.

Rupp, M.E. et al., "Characterization of the Importance of Polysaccharide Intercellular Adhesin/Hemagglutinin of *Staphylococcus epidermidis* in the Pathogenesis of Biomaterial-Based Infection in a Mouse Foreign Body Infection Model", *Infection and Immunity*, May 1999, pp. 2627-2632, vol. 67, No. 5, American Society for Microbiology.

Rupp, M.E. et al., "Characterization of *Staphylococcus epidermidis* Polysaccharide Intercellular Adhesin/Hemagglutinin in the Pathogenesis of Intravascular Catheter-Assocated Infection in a Rat Model", *Infection and Immunity*, May 1999, pp. 2656-2659, vol. 67, No. 5, American Society for Microbiology.

Sanford, B.A. et al., "Detection of Staphylococcal Membrane Receptors on Virus-Infected Cells by Direct Adhesin Overlay", *Infection and Immunity*, Jun. 1986, pp. 671-675, vol. 52, No. 3, American Society for Microbiology.

Takeda, S. et al., "Protection Against Endocarditis Due to *Staphylococcus epidermidis* by Immunization with Capsular Polysaccharide/Adhesin", *Circulation*, Dec. 1991, pp. 2539-2546, vol. 84, No. 6.

Tojo, M. et al., "Isolation and Characterization of a Capsular Polysaccharide Adhesin from *Staphylococcus epidermidis*", *The Journal of Infectious Diseases*, Apr. 1988, pp. 713-722, vol. 157, No. 4, The University of Chicago.

Tollersrud, T. et al., "Genetic and Serologic Evaluation of Capsule Production by Bovine Mammary Isolates-of *Staphylococcus aureus* and Other *Staphylococcus* spp. from Europe and the United States", *Journal of Clinical Microbiology*, Aug. 2000, pp. 2998-3003, vol. 38, No. 8, American Society for Microbiology.

Vershigora, A.E. et al., "Secretory Antibodies to Homologous and Heterologous Staphylococcal Strains in the Colostrum of Rabbits", *ZH Mikrobiol Epidermoil Immunobiol*, 1980, pp. 88-90 Abstract, vol. 0, No. 10 (Rec'd 1981).

Wray, S.K. et al., "Identification and Characterization of a Uroephithelial Cell Adhesin from a Uropathogenic Isolate of *Proteus mirabilis*", *Infection and Immunity*, Oct. 1986, pp. 43-49, vol. 54, No. 1, American Society for Microbiology.

Yamada, T. et al., "Possible common biological and immunological properties for detecting encapsulated strains of *Staphylococcus epidermidis*", *J. Clin. Microbiol.*, Oct. 1988, pp. 2167-2172 Abstract, vol. 25, No. 10.

Yoshida, K. et al., "Mouse Virulent Strain of *Staphylococcus epidermidis*-Relation of Antiphagocytic Activity to the Protection-Inducing Antigen", *J. Microbiol.* (Japan), 1976, pp. 209-217, vol. 20, No. 3.

Yoshida, K. et al., "Immunological response to a strain of *Staphylococcus epidermidis* in the rabbit: production of protective antibody", *J. Med. Microbiol.*, Nov. 1978, pp. 371-377 Abstract, vol. 11, No. 4.

Youmans, G.P. et al., "Staphylococci, Staphylococcal Disease, and Toxic Shock Syndrome", *The Biologic and Clinical Basis of Infectious Diseases, Third Edition*, 1985, pp. 618-629, and 738-739.

Ziebuhr, W. et al., "A novel mechanism of phase variation of virulence in *Staphylococcus epidermidis*: evidence of control of the polysaccharide intercellular adhesin synthesis by alternating insertion and excision of the insertion sequence element IS256", *Molecular Microbiology*, 1999, pp. 345-356, vol. 32, No. 2, Blackwell Science Ltd.

Fattom, Ali, "Effect of conjugation methodology, carrier protein, and adjuvants on the immune response to *Staphylococcus auerus* capsular polysaccharides", Vaccine, 13(14): 1288-1293, 1995.

Fournier, J., et al. , "Purification and Characterization of *Staphylococcus aureus* . . . ", *Infection and Immunity*, (1984), 45:1:87-93.

Gerke, J., et al., "Experimental *Pseudomonas aeruginosa* Infection of the Mouse Cornea", *Infection and Immunity*, (1971), 3:2:209-216.

Heilmann, C., et al., "Characterization of Tn917 Insertion Mutants of *Staphylococcus epidermidis* Affected in Biofilm Formation", (1996), 64:1:277-282.

Ichiman, Y., et al., "Induction of Resistance with heat-Killed Unencapsulated Strains of *Staphylococcus epidermidis* against Challenge with Encapsulated Strains of *Staphylococcus epidermidis*", *Microbiol. Immunol.*, (1989), 33:4:277-286.

Ichiman, Y., et al., "Relation of human serum antibody against *Staphylococcus epidermidis* cell surface polysaccharide detected by enzyme-linked immunosorbent assay to passive protection in the mounse", *J Applied Bacteriology*, (1991), 71:176-181.

Ichiman, Y., et al., Specificity of Monoclonal Antibodies Against an Encapsulated Strain of *Staphylococcus epidermids*:, *The Staphylococci, Zbl. Bakt. Suppl. 21*, (1991), 150-152.

Ichiman, Y., et al., The Relationship fo Capsular-type of *Staphylococcus epidermidis* to Virulence and Induction of Resistance in the Mounse, *J Applied Bacteriology*, (1981), 51:229-241.

Kojima, Yoshifumi, et al., "Antibody to the Capsular Polysaccharide/Adhesin Protects Rabbits against Catheter-Related Bacterimia Due to Coagulase-Negative Staphylococci", J Infectious Disease, 162:435-441, 1990.

Lee, J.C. et al., Chemical characterization and immunogenicity of capsular polysaccharide isolated from mucoid *Staphylococcus aureus*, Infection and Immunity, 55(9):2191-2197, 1987.

Mack, D., et al., "Association of Biofilm Production of Coagulase-Negative Staphylococci with Expression of a Specific Polysaccharide Intercellular Adhesin", *J Infectious Disease*, (1996), 174:881-884.

Mack, D., et al., "Characterization of Transposon Mutants of Biofilm-Producing *Staphylococcus epidermidis* Impaired in the Accumulative Phase of Biofilm Production:Genetic Identification of a Hexosamine-Containing Polysaccharide Intercellular Adhesin", *Infection and Immunity*, (1994), 62:8:3244-3253.

Mack, D., et al., "Parallel Induction by Glucose of Adherence and a Polysaccharide Antigen Specific for Plastic-Adherent *Staphylococcus epidermidis*: Evidence for Functional Relation to Intercellular Adhesion", *Infection and Immunity*, (1992), 60:5:2048-2057.

Moreau, M., et al., "Structure of the type 5 capsular polysaccharide of *Staphylococcus aureus*", *Carbohydrate Research*, (1990), 201:285-297.

Ohshima, Y., et al., "Cell Surface Antigen of Encapsulated *Staphylococcus epidermidis* ATCC 31432", *J Clinical Microbiology*, (1987), 25:7:1338-1340.

Ohshima, Y., et al., "Protection Inducing Antigen of an Encapsulated *Staphylococcus epidermidis* SE-10", *The Staphylococci, Zbl. Bakt. Suppl. 21*, (1991), 279-280.

Schumacher-Perdreau, F., et al., "Comparative analysis of a biofilm-forming *Staphylococcus epidermids* strain and its adhesion-positive, accumulation-negative mutant M7", *FEMS Microbiology Letters*, (1994), 117:71-78.

Sompolinsky, D., et al., "Encapsulation and Capsular Types in Isolates of *Staphylococcus aureus* from Different Sources and Relationship to phage Types", *J Clinical Microbiology*, 22:5:824-834.

Thomas, V., et al., "Enzyme-Linked Lectinsorbent Assay Measures N-Acetyl-D-Glucosamine in Matrix of Biofilm Produced by *Staphylococcus epidermidis*", *Current Microbiology*, (1997), 35:249-254.

Wessels, M., et al., "Isolation and Characterization of Type IV Group B Streptococcus Capsular Polysaccharide", Infection and Immunity, 57(4): 1089-1094, 1989.

Yoshida, K., et al., "Cross Protection between a strain of *Staphylococcus epidermidis* and eight other species of coagulase-negative staphylococci", Can J Microbiol. (1988), 34:913-915.

Ziebuhr, W., et al., "Detection of the Intercellular Adhesion Gene Cluster (ica) and phase Variation in *Staphylococcus epidermidis* Blood Culture Strains and Mucosal Isolates", Infection and Immunity, (1997), 65:3:890-896.

GENBANK Submission; NIH/NCBI, Accession No. BA000018; Kuroda et al.; Oct. 22, 2004 (last submission).

[No Author Listed] ATCC Catalogue website 2001; ATCC No. 35984.

[No Author Listed] ATCC Catalogue: Bacteria and Bacteriophages; 1992; 18th Edition; p. 301.

Conlon et al., icaR encodes a transcriptional repressor involved in environmental regulation of ica operon expression and biofilm formation in *Staphylococcus epidermidis*. J Bacteriol. Aug. 2002;184(16):4400-8.

Conlon et al., Regulation of icaR gene expression in *Staphylococcus epidermidis*. FEMS Microbiol Lett. Nov. 5, 2002;216(2):171-7.

Götz, Staphylococcus and biofilms. Mol Microbiol. Mar. 2002;43(6):1367-78.

Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.

Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004;186(8):2449-56.

Kelly-Quintos et al., Biological Characterization of Fully Human Monoclonal Antibodies to Staphylococcal Surface Polysaccharide PNAG. Abstracts of the 104th General Meeting of the American Society for Microbiology. Am Soc Microbiol. May 2004;abstract A-63. Abstract and corresponding presentation.

Kohler, Derivation and diversification of monoclonal antibodies. Science. Sep. 19, 1986;233(4770):1281-6.

Kuroda et al., Whole genome sequencing of meticillin-resistant *Staphylococcus aureus*. Lancet. Apr. 21, 2001;357(9264):1225-40.

Maira-Litran et al., Immunochemical properties of the staphylococcal poly-N-acetylglucosamine surface polysaccharide. Infect Immun. Aug. 2002;70(8):4433-40.

Maira-Litran et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Abstract Only.

Maira-Litran et al., Deacetylated-poly-N-acetyl Glucosamine (dPNAG) Polysaccharide Conjugated to Diphtheria Toxoid (DT) Confers Protection Against Multiple Strains of *Staphylococcus aureus* in a Murine Model of Bacteremia. Abstracts of the 104th General Meeting of the American Society for Microbiology. Am Soc Microbiol. May 2004;abstract D-130. Abstract and corresponding presentation.

Maira-Litran et al., Synthesis and Immunological Properties of a Staphylococcal Deacetylated-poly-N-acetyl Glucosamine (dPNAG) Polysaccharide and Clumping Factor A (ClfA) Protein Conjugate Vaccine. Abstracts of the 104th General Meeting of the American Society for Microbiology. Am Soc Microbiol. May 2004;abstract E-062. Abstract and corresponding presentation.

Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23):1893-916.

Milstein, From antibody structure to immunological diversification of immune response. Science. Mar. 14, 1986;231(4743):1261-8.

Vuong et al., A crucial role for exopolysaccharide modification in bacterial biofilm formation, immune evasion, and virulence. J Biol Chem. Dec. 24, 2004;279(52):54881-6. Epub Oct. 22, 2004.

Wang et al., The pgaABCD locus of *Escherichia coli* promotes the synthesis of a polysaccharide adhesin required for biofilm formation. J Bacteriol. May 2004;186(9):2724-34.

Allignet et al., Tracking adhesion factors in *Staphylococcus caprae* strains responsible for human bone infections following implantation of orthopaedic material. Microbiology. Aug. 1999;145 ( Pt 8):2033-42.

Arciola et al., In catheter infections by *Staphylococcus epidermidis* the intercellular adhesion (ica) locus is a molecular marker of the virulent slime-producing strains. J Biomed Mater Res. Mar. 5, 2002;59(3):557-62. Abstract Only.

Bhasin et al., Identification of a gene essential for O-acetylation of the *Staphylococcus aureus* type 5 capsular polysaccharide. Mol Microbiol. Jan. 1998;27(1):9-21. Abstract Only.

Cramton et al., Anaerobic conditions induce expression of polysaccharide intercellular adhesin in *Staphylococcus aureus* and *Staphlococcus epidermidis*. Infect Immun. Jun. 2001;69(6):4079-85.

Dobinsky et al., Influence of Tn917 insertion on transcription of the icaADBC operon in six biofilm-negative transposon mutants of *Staphylococcus epidermidis*. Plasmid. Jan. 2002;47(1):10-7. Abstract Only.

Fattom et al., Antigenic determinants of *Staphylococcus aureus* type 5 and type 8 capsular polysaccharide vaccines. Infect Immun. Oct. 1998;66(10):4588-92.

Fey et al., Characterization of the relationship between polysaccharide intercellular adhesin and hemagglutination in *Staphylococcus epidermidis*. J Infect Dis. Jun. 1999;179(6):1561-4. Abstract Only.

Fowler et al., The intercellular adhesin locus ica is present in clinical isolates of *Staphylococcus aureus* from bacteremic patients with infected and uninfected prosthetic joints. Med Microbiol Immunol (Berl). Apr. 2001;189(3):127-31. Abstract Only.

Frebourg et al., PCT-Based assay for discrimination between invasive and contaminating *Staphylococcus epidermidis* strains. J Clin Microbiol. Feb. 2000;38(2):877-80.

Gelosia et al., Phenotypic and genotypic markers of *Staphylococcus epidermidis* virulence. Clin Microbiol Infect. Apr. 2001;7(4):193-9. Abstract Only.

Heilmann et al., Further characterization of *Staphylococcus epidermidis* transposon mutants deficient in primary attachment or intercellular adhesion. Zentralbl Bakteriol. Jan. 1998;287(1-2):69-83. Abstract Only.

Ji et al., Regulated antisense RNA eliminates alpha-toxin virulence in *Staphylococcus aureus* infection. J Bacteriol. Nov. 1999;181(21):6585-90.

Ji et al., Identification of critical staphylococcal genes using conditional phenotypes generated by antisense RNA. Science. Sep. 21, 2001;293(5538):2266-9.

Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.

Longworth et al., O-Acetylation status of the capsular polysaccharides of serogroup Y and W135 meningococci isolated in the UK. FEMS Immunol Med Microbiol. Jan. 14, 2002;32(2):119-23. Abstract Only.

Mack et al., Molecular mechanisms of *Staphylococcus epidermidis* biofilm formation. J Hosp Infect. Dec. 1999;43 Suppl:S113-25. Abstract Only.

Mack et al., Genetic and biochemical analysis of *Staphylococcus epidermidis* biofilm accumulation. Methods Enzymol. 2001;336:215-39.

McNeely et al., Antibody responses to capsular polysaccharide backbone and O-acetate side groups of Stretococcus pneumoniae type 9V in humans and rhesus macaques. Infect Immun. Aug. 1998;66(8):3705-10.

Michon et al., Structure activity studies on group C meningococcal polysaccharide-protein conjugate vaccines: effect of O-acetylation on the nature of the protective epitope. Dev Biol (Basel). 2000;103:151-60. Abstract Only.

Muller et al., Capsular polysaccharide/adhesin (PS/A) production by coagulase-negative staphylococci (CNS) is associated with adherence to silastic tubing. 1989. p. 49. Abstract B-111.

Ohshima et al., "Zentralbl Bakteriol." 274(3), (1990), p. 417-425. "*Staphylococcus hyicus, Staphylococcus epidermis*, Protection, Bacterial Morphology." 1.8.21, p. 584-591.

\* cited by examiner

ACTIVE IMMUNITY: SIGNIFICANT DIFFERENCE NOTED BETWEEN PS/A AND T3 IMMUNIZED SWISS WEBSTER MICE (n=5, $p \leq 0.037$).

PASSIVE IMMUNITY: SIGNIFICANT DIFFERENCE NOTED BETWEEN ANTI-PS/A AND ANTI-T3 IMMUNIZED SWISS WEBSTER MICE (n=5, p ≤ 0.0002).

Gel#

| Date: | Descript.: | | |
|---|---|---|---|
| | | V/A: | |
| | | Agar%: | 0.7 |
| | | Time: | |
| | | Temp.: | RT |

1. MARKER 1kb LADDER
2. NO DNA    20μl
3. icaA-C
4. RP62A
5. MN8
6. MN8-MUC.
7. RN450
8. REYNOLDS
9. BECKER
10. 1A
11.
12.
13.
14.
15.
16.
17.
18.
19.
20.
21.
22.
23.
24.
25.
26.
27.
28.
29.
30.
31.
32.

RELOADED GEL WITH REDUCING CORE OF PCR PRODUCT FROM icaA-C, RP62A AND RN450.

SEQUENCE LISTING

<160> NUMBER OF SEQ ID NOS: 3

<210> SEQ ID NO 1
<211> LENGTH: 4500
<212> TYPE: DNA
<213> ORGANISM: Staphylococcus Epidermidis

<400> SEQUENCE: 1

| | | | | | |
|---|---|---|---|---|---|
| tttgaaatct | cgaatttgtt | acatactagt | tacaaaaatt | atttttttaa | aaatacattt | 60 |
| aacagtgaat | atacttggtc | tttaaaacgg | tttttactgt | cctcaataat | cccgaatttt | 120 |
| tgtgaaaagg | aggctctaaa | ataccaagtc | tcaagaaaaa | gaagaattaa | gtttataaag | 180 |
| tcctctttat | ccaaagcgat | gtgcgtagga | tcataatact | ttatcaattc | atcatgtaag | 240 |
| gtagtattaa | tttcttgaag | atggtgtttg | atttctgaat | tcagtgcttc | tggagcacta | 300 |
| gataattgaa | catataattt | aatatatctc | tcatcaacgt | cgaatataaa | tttgaataaa | 360 |
| aactggtaaa | gtccgtcaat | ggaataatta | tcatcatggt | tcctaagcaa | aaaatctata | 420 |
| aagtaattga | aacaattctc | aacactttt | cgatatattt | cttccttatt | atcgtaatga | 480 |
| taatatagac | tagccttttt | tatatttaca | cttttagaaa | tatcatcaag | tgtagtacca | 540 |
| tcgtacccct | tttcggaaaa | taaggttatt | gcgttatcaa | taatcttatc | tttcaattct | 600 |
| aaaatctccc | ccttattcaa | ttttctaaaa | atatattaca | gaaaaattaa | gttaaaatta | 660 |
| caaatattac | tgtttcagta | taacaacatt | ctattgcaaa | ttgaaatact | ttcgattagc | 720 |
| atatgctttta | caacctaact | aacgaaaggt | aggtgaaaaa | atgcatgtat | ttaactttt | 780 |
| acttttctat | ccaattttta | tgtcaattta | ctggatagta | ggatcgattt | actattttt | 840 |
| tattaaagaa | aaacccttta | atcgatcatt | gttagtaaaa | tctgaacatc | aacaagttga | 900 |
| aggcatctcc | tttttattag | cttgctacaa | tgaaagtgaa | acagttcaag | acacgctttc | 960 |
| tagtgttta | tctctagaat | atcctgaaaa | agaaattatc | attatcaatg | atggaagttc | 1020 |
| tgataatact | gctgaaatca | tctatgactt | caagaaaaat | catgatttta | aatttgttga | 1080 |
| cctcgaagtc | aatagaggta | agctaatgc | actcaatgag | ggaatcaaac | aagcatctta | 1140 |
| cgaatatgtt | atgtgtttag | atgctgacac | tgtcattgat | gacgatgcgc | ctttttatat | 1200 |
| gattgaagac | tttaaaaaga | atccaaaatt | aggcgcagtt | acaggtaatc | cacgtattcg | 1260 |
| taataaaagt | tctattttag | gaaaaataca | gaccattgaa | tatgcaagta | ttattggttg | 1320 |
| tatcaagcga | agtcaatctc | ttgcaggagc | aatcaatact | atttcaggtg | ttttcacact | 1380 |
| atttaaaaaa | agtgcactca | agatgtagg | ttattgggat | actgacatga | ttactgagga | 1440 |
| tattgctgtt | tcatggaaac | tccatctttt | tgattacgaa | attaagtacg | aaccacgtgc | 1500 |
| tctatgctgg | atgttagtgc | ctgaaactat | aggtggttta | tggaaacaaa | gggttcgatg | 1560 |
| ggctcaaggc | gggcatgaag | tacttttaag | agacttttgg | ccaacaatta | aaactaagaa | 1620 |
| attatcacta | tatattttaa | tgtttgaaca | aatcgcatcg | attacatggg | tctacatcgt | 1680 |
| actatgttat | ttatcttttt | tagtaatcac | agccaacatc | ttagattaca | catatttaaa | 1740 |
| atatagtttt | tcaatctttt | tcttttcatc | ctttacgatg | acctttatca | atatcatcca | 1800 |
| atttacagtt | gccttattta | ttgacagtcg | ctacgaaaag | aaaaatatag | ttggcctgat | 1860 |
| atttttaagt | tggtatccaa | cgttatactg | ggttatcaat | gccgcagttg | tcattatggc | 1920 |
| atttcctaaa | gcattaaaaa | gaaagaaagg | tggctatgct | acatggtcaa | gcccagacag | 1980 |
| aggcaatatc | caacggtaac | ctcttatta | aatatagtta | gggagagctt | atttattact | 2040 |

-continued

```
atatccggag tatttggat gtattgtatc gttgtgatga ttgtttatat aggaactctt    2100
atcaattctc aaatggaaag tgttataaca atacgtattg cattaaatgt tgaaaacacg    2160
gaaatttaca aattattcgg atggatgagt ttgtttgtac ttattatatt tatctttttt    2220
acatttagtc tcgcgtttca aaaatataag aaaggtcgtg acatatgaaa cctttcaaat    2280
taatctttat tagcgcattg atgatattaa taatgacgaa tgcaacacca atatcacacc    2340
tgaatgctca agctaatgaa gaaaacaaga agttaaagta cgaaaaaaat agcgcactcg    2400
cgttaaaacta tcacagagta agaaaaaagg atcctttgaa tgactttata tcattactat    2460
ctgggagtaa ggaaattaaa aattatagtg tcactgatca agaatttaaa tcacaaattc    2520
aatggcttaa agcacacgac gcaaagtttt taactttgaa agaatttatt aaatataaag    2580
aaaaaggtaa atttcctaaa agaagtgttt ggattaactt tgatgatatg gatcaaacga    2640
tttatgacaa tgccttccct gttttgaaaa aatatcatat tccagcaaca ggttttctta    2700
ttacgaacca cattggttct accaattttc ataatttaaa tttactttca aaaaagcaat    2760
tagatgaaat gtatgaaaca ggcttatggg actttgaatc tcatactcat gatttacacg    2820
ctcttaagaa aggcaataaa tcgaagtttt tagattcgtc tcaatctgtt gctagtaaag    2880
atattaaaaa aagcgaacac tatttaaata aaaactaccc aaaaaatgaa cgcgcacttg    2940
cttacccata cggattaatt aatgacgaca aaataaaagc tatgaaaaaa aatggaattc    3000
aatatgggtt tacacttcag gaaaaagctg tcacaccaga tgccgataac tatagaattc    3060
cacgtatttt agtaagtaat gatgcatttg aaacgctaat aaaggaatgg gacggattcg    3120
atgaagaaaa ataaacttga attagtgtat ttacgtgcgt ttatttgtgt cataatcatc    3180
gtgacacact tactaacgca aatcacttta gaaaatgaac agatgtctga tagttcactc    3240
atattgcaat attatatacg caatattttt attttcggca cccctagttt tataatattg    3300
tctcaattat taacaacatt aaattacgaa tcagtaacta taaattatct ttttcaaga    3360
tttaagtata ttttattcc atatctttta atcggcttgt tctatagtta tagtgaatca    3420
cttatcaccg cttcttcttt taaaaagcag tttatcgaaa atgttgtttt aggacaatgg    3480
tatggctatt tcattatcat aattatgcag ttctttgttc tatcttatat catttacaaa    3540
attaatttta gattgttcaa tagtaaaatt ttgctgcttt tagcatttat agtccaacaa    3600
tcttatctac attatttttt gaataatgac acttttcatc aattcatgac tcattattat    3660
ccattaagcg aaaatacaat gatattagga tggatattct acttttttctt aggtggttac    3720
attggctata attatgaaaa aatattatct ttcttagaaa aatatttaat tatagttatt    3780
atgttaactt taggcgcata tgttttattt atcgctgttt ccggtagtga ttattggaat    3840
gtcacaagct ttacttatac gttaacatta tataatagtg tcatgttctt cttattacta    3900
ggagtctgta tgcactttaa aactatgtta ttaaatacta ttaaagctat tagtgcattt    3960
tccttttca tttatttgtt gcacccaatt atcttagatt ctcttttgc ttacaccaac    4020
atatttgaag ataatacaat tgttttcttg gcgatttcac ttttaatgat tctaggaatt    4080
tgtataggcg tcggaatgat gttaagagag ttttatatat tcagatttgt aattggaaaa    4140
caaccgtaca agttacaatt tgaccaatac cagcctaact ggaattaata aaaaaagtcc    4200
cttattcaag ctatggctta tgtatgtgct tgaataaggg attttatctt actatagttt    4260
cacattatga aaataatttt tttaatattc tgtataaaga gcctaataat tgaaagaaat    4320
cacctgtcat gtatctcact cctatctata taagattacg ttaggtttat accctatatc    4380
```

-continued

```
attttattta tttgttgatg ttaattgttc actttgtact aaatcatcag caagaccatg    4440
ccaaaactgt tgcaattcat ctctagtacg ttttgtatct gtactgtctt gtcctacaaa    4500

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgcactcaat gagggaatca                                                  20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
aatcactacc ggaaaacagc g                                                21
```

POLYSACCHARIDE VACCINE FOR STAPHYLOCOCCAL INFECTIONS

RELATED APPLICATIONS

This application is a continuation in part of U.S. Ser. No. 09/399,904 filed on Sep. 21, 1999 and entitled Polysaccharide Vaccine for *Staphylococcal* Infections, now abandoned, which is a continuation in part of U.S. Ser. No. 09/354,408 filed on Jul. 15, 1999 and entitled Polysaccharide Vaccine for *Staphylococcal* Infections, now abandoned, which claims priority to U.S. Provisional Patent Application No. 60/093,117, filed Jul. 15, 1998, the entire contents of which are hereby incorporated by reference.

GOVERNMENT SUPPORT

The present invention was supported in part by a grant from the United States National Institutes of Health AI23335. The U.S. Government may retain certain rights in the invention.

FIELD OF THE INVENTION

The present invention relates to polysaccharide compositions useful for inducing immunity for the prevention and treatment of *staphylococcal* infections. The invention also relates to methods of making and using polysaccharide based antigens, related antibodies and diagnostic kits and for inducing active and passive immunity using the polysaccharide material and antibodies thereto.

BACKGROUND OF THE INVENTION

*Staphylococci* are gram-positive bacteria which normally inhabit and colonize the skin and mucus membranes of humans. If the skin or mucus membrane becomes damaged during surgery or other trauma, the *staphylococci* may gain access to internal tissues causing infection to develop. If the *staphylococci* proliferate locally or enter the lymphatic or blood system, serious infectious complications such as those associated with *staphylococcal* bacteremia may result. Complications associated with *staphylococcal* bacteremia include septic shock, endocarditis, arthritis, osteomyelitis, pneumonia, and abscesses in various organs.

*Staphylococci* include both coagulase positive organisms that produce a free coagulase and coagulase negative organisms that do not produce this free coagulase. *Staphylococcus aureus* is the most common coagulase-positive form of *staphylococci*. *S. aureus* generally causes infection at a local site, either extravascular or intravascular, which ultimately may result in bacteremia. *S. aureus* is also a leading cause of acute osteomyelitis and causes a small number of *staphylococcal* pneumonia infections. Additionally, *S. aureus* is responsible for approximately 1–9% of the cases of bacterial meningitis and 10–15% of brain abscesses. There are at least twenty-one known species of coagulase-negative *staphylococci*, including *S. epidermidis*, *S. saprophyticus*, *S. hominis*, *S. warneri*, *S. haemolyticus*, *S. saprophiticus*, *S. cohnii*, *S. xylosus*, *S. simulans*, and *S. capitis*. *S. epidermidis* is the most frequent infection-causing agent associated with intravenous access devices and the most frequent isolate in primary nosocomial bacteremias. *S. epidermidis* is also associated with prosthetic valve endocarditis.

*Staphylococcus* is also a common source of bacterial infection in animals. For instance, *staphylococcal* mastitis is a common problem in ruminants including cattle, sheep, and goats. The disease is generally treated with antibiotics to reduce the infection but the treatment is a costly procedure and still results in a loss of milk production. The most effective vaccines identified to date are live, intact *S. aureus* vaccines administered subcutaneously. The administration of live vaccines, however, is associated with the risk of infection. For that reason, many researchers have attempted to produce killed *S. aureus* vaccines and/or to isolate capsular polysaccharides or cell wall components which will induce immunity to *S. aureus*. None of these attempts, however, has been successful.

*S. aureus* includes a cell wall component composed of a peptidoglycan complex which enables the organism to survive under unfavorable osmotic conditions and also includes a unique teichoic acid linked to the peptidoglycan. External to the cell wall a thin polysaccharide capsule coats most isolates of *S. aureus*. This serologically distinct capsule can be used to serotype various isolates of *S. aureus*. Many of the clinically significant isolates have been shown to include two capsular types, CP5 and CP8.

Type CP5 has the following chemical structure:

→4)-β-D-ManpNAcA3Ac-(1→4)-α-L-FucpNAc-
(1→3)-β-D-FucpNAc-(1→

Type CP8 has the following chemical structure:

→3)-β-D-ManpNAcA4Ac-(1→3)-α-L-FucpNAc-
(1→3)-β-D-FucpNAc-(1→

Studies on over 1600 *S. aureus* isolates showed that 93% were of either type 5 or type 8 capsular polysaccharides. Additionally, more than 80% of the *S. aureus* isolated from sheep, goats, and cows with mastitis and chickens with osteomyelitis have been demonstrated to include at least one of these two capsular types. Although CP5 and CP8 are structurally similar, they have been demonstrated to be immunologically distinct.

SUMMARY OF THE INVENTION

The present invention relates to methods and products useful for immunization of humans and animals against infection by coagulase-negative and coagulase-positive *staphylococci*. It has been discovered, according to the invention, that a true "capsule" of *S. aureus* extends out beyond the CP5 or CP8 layer or is produced instead of the CP5 or CP8 layer. This material, which is referred to as the capsular polysaccharide/adhesin antigen (also referred to herein as PS/A), has been purified to near homogeneity and the structure identified. The native PS/A which can be isolated from *Staphylococci* such as *S. aureus* and *S. epidermis* is a high molecular weight polyglucosamine which is heavily substituted with acetate residues, and is referred to as a poly-β-1-6-N-acetylglucosamine. The isolated and purified PS/A has been found to be highly immunogenic in vivo.

In one aspect the invention relates to pure PS/A antigens. One example of a pure PS/A is defined by the following structure:

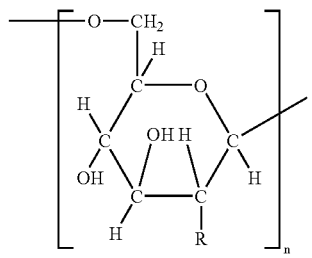

wherein n is an integer greater than or equal to 300, wherein R is selected from the group consisting of —NH—CO—$(CH_2)_m$—COOH, —NH—CO—$CH_3$, and —$NH_2$, wherein m is 1–5, and wherein at least 50% of the R groups are —NH—CO—CH$_3$ and having a molecular weight of at least 100,000 Daltons. In some embodiments n is an integer of greater than or equal to 490.

In some embodiments the antigen consists of the following structure:

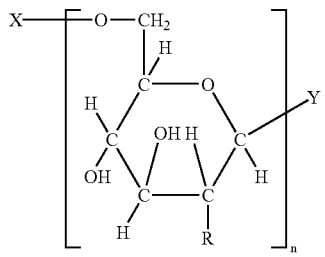

wherein X is either H, a carrier compound, or a linker joined to a carrier compound; and Y is either OH, a carrier compound or a linker joined to a carrier compound.

In other examples the isolated PS/A, is a polysaccharide having at least 300 monomeric units, at least 50% of which are substituted with acetate, the antigen having a molecular weight of at least 100,000 Daltons, and wherein at least 50% of the units are β-1,6-glucosamine units. In some embodiments all of the units are β-1,6-glucosamine units. In other embodiments the remaining units are selected from the group consisting of α-1-6 polyglucose, α-1-4 polyglucose, α-1-3 polyglucose, β-1-4 polyglucose, β-1-3 polyglucose, and α1-4 polygalactose. In yet other embodiments at least some of the remaining units have a polymer backbone in a β-1,6 formation, a β-1,4 formation, or a α-1,3 formation.

In another example the PS/A is one which is made by preparing an impure PS/A from a bacterial culture, incubating the impure PS/A with an acid or a base to produce a semi-pure PS/A preparation; neutralizing the preparation, and incubating the neutralized preparation in hydrofluoric acid to produce the PS/A. In one embodiment the bacterial culture is a *Staphylococcus aureus* culture. In another embodiment the bacterial culture is a coagulase negative *Staphylococci* culture.

In some embodiments the PS/A is formulated as a vaccine.

In other embodiments the PS/A also includes at least one carrier compound conjugated to the PS/A or alternatively no carrier compound is present. The carrier compound optionally may be conjugated to the PS/A through a linker. In some embodiments the carrier compound is a peptide carrier.

In some embodiments the PS/A is at least 95% pure, at least 97% pure, or at least 99% pure. In yet other embodiments the PS/A is substantially free of phosphate or teichoic acid.

According to other aspects of the invention, the PS/A comprises the following structure:

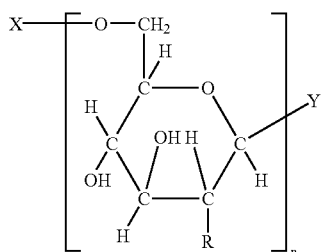

wherein n is at least 3, wherein R is selected from the group consisting of —NH—CO—(CH$_2$)$_m$—COOH, —NH—CO—CH$_3$, and —NH$_2$, wherein m is 1–5, provided that at least 50% of the R groups are —NH—CO—CH$_3$, wherein X is either H, a carrier compound, or a linker joined to a carrier compound; Y is either OH, a carrier compound or a linker joined to a carrier compound, provided that when X is H, Y is not OH, and wherein when the carrier compound is a polysaccharide it is not an N-acetyl β 1-6 glucosamine. Thus, the pure PS/A contains a polysaccharide epitope region of at least 3 sugars in length and may contain additional groups such as additional sugar groups (including polysaccharide groups) and carrier peptides that do not prevent antigen from binding to an antibody that recognizes the epitope. In some embodiments the antigen contains less than 5% or less than 1% galactose. In other embodiments n is 3–20 or 3–6.

In some embodiments X is a carrier molecule and wherein the carrier molecule is a polysaccharide, provided that X may be optionally substituted directly, or through a linker, with one or more carrier peptides. In other embodiments X is a carrier peptide.

Y, in other embodiments, is a carrier molecule and wherein the carrier molecule is a polysaccharide, provided that Y may be optionally substituted directly, or through a linker, with one or more carrier peptides. In yet other embodiments Y is a carrier peptide.

The antigens of the invention, in some aspects are at least 50% acetylated. In various embodiments the antigens are at least 55%, 60%, 65%, 60%, 75%, 80%, 85%, 90%, 95%, or 100% acetylated and/or at least 55%, 60%, 65%, 60%, 75%, 80%, 85%, 90%, 95%, or 100% of the R groups are —NH—CO—CH$_3$.

In some aspects of the invention the PS/As have a molecular weight of greater than 30,000 Daltons. In more preferred embodiments the PS/As have a molecular weight of greater than 40,000; 50,000; 60,000; 70,000; 80,000; 90,000; or 100,000 Daltons. In certain embodiments the PS/As have a molecular weight of greater than 100,000, 150,000, 200,000, or 250,000 Daltons. In other embodiments the PS/As have a molecular weight of between 100,000 and 5,000,000 Daltons or any integer range therebetween.

In one embodiment the antigen may be substituted with a single type of R group substituent or by more than one type of R group substituent. When the antigen is substituted with a single type of R group substituent the antigen is a homo-substituted polymer. In these embodiments the antigen is substituted with acetate. When the antigen is substituted with more than a single type of R group substituent the antigen is a hetero-substituted polymer.

The invention in other aspects encompasses a composition comprising any of the antigens of the invention and a pharmaceutically acceptable carrier. In other aspects the invention is a vaccine component made by conjugating a PS/A described herein, including the different embodiments, to a carrier compound, directly or through a linker. Another aspect of the invention describes a method of making a vaccine component comprising conjugating a PS/A described herein, including the different embodiments, to a carrier compound, directly or through a linker.

According to other aspects, the invention is a method of preparing a polysaccharide antigen by preparing an impure PS/A from a bacterial culture, incubating the impure PS/A with a base or acid to produce a semi-pure PS/A preparation; neutralizing the preparation, and treating the neutralized preparation to produce the PS/A. In some embodiments the impure PS/A is incubated with a base, neutralized with an acid, and then treated with hydrofluoric acid to produce a pure PS/A. In other embodiments the impure PS/A is incubated with a base or an acid and neutralized with an acid or base, respectively. Optionally, this preparation is then treated by dialysis against deionized water, lyophilized and resuspended in a buffer.

In yet other aspects, the invention is a method for preventing infection by *staphylococcus* in a subject. The invention involves administering to a non-rodent subject an effective amount for inducing an immune response against *staphylococcus* of any of the antigens of the invention. In some embodiments the *staphylococcus* is *staphylococcus aureus* and in other embodiments the *staphylococcus* is *staphylococcus epidermidis*.

The subject is any subject which can be infected with *staphylococcus* and which is not a rodent. In some embodiments the non-rodent subject is a human subject and in other embodiments the non-rodent subject is a primate, horse, cow, swine, goat, sheep, chicken, dog, or cat. In some embodiments the subject is a human over 60 years of age, the subject is healthy.

Preferably the antigen induces active immunity against poly β 1-6-N-acetylglucosamine and is at least about 75% pure and/or less than 10% galactose is present in the preparation containing the antigen. In different embodiments the antigen is at least about 92%, 95%, or 97% pure and/or less than 5% or 1% galactose is present in the preparation containing the antigen.

In some embodiment the non-rodent subject is a subject at risk of exposure to *staphylococcus* and in other embodiments the non-rodent subject is a subject which has been exposed to *staphylococcus*.

The invention in other aspects is a method for preventing infection by *staphylococcus* in a subject by administering to a non-rodent subject an effective amount for inducing an immune response against *staphylococcus* of a pure PS/A having the following structure:

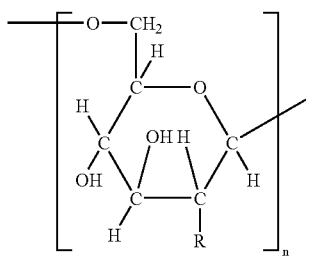

wherein n is at least 3, wherein R is selected from the group consisting of —NH—CO—(CH$_2$)$_m$—COOH, —NH—CO—CH$_3$, and —NH$_2$, wherein m is 1–5, provided that at least 50% of the R groups are —NH—CO—CH$_3$. In some aspects of this method, the subject has not received a medical device implant and/or the antigen is administered systemically to the subject.

Optionally the antigen may be administered in conjunction with an adjuvant and/or the antigen may conjugated to a carrier compound in any of the methods. In some embodiments the carrier compound is a peptide carrier.

A method for generating antibodies is provided according to another aspect of the invention. The method involves administering to a subject an effective amount for producing antibodies specific for *staphylococcus* of any of the antigens of the invention and an adjuvant, and isolating antibodies from the subject. In one embodiment the method also includes the step of manipulating the antibodies to generate monoclonal antibodies.

According to yet another aspect of the invention a method of identifying a monoclonal antibody against a PS/A is provided. The method involves inducing an immune response in a non-human subject to the antigen, isolating antibody producing cells from said subject, producing immortalized cells from said antibody producing cells, testing the ability of said immortalized cells to produce said monoclonal antibody using any of the antigens of the invention. The method, in one embodiment, also includes the step of making a monoclonal antibody by purifying said monoclonal antibody produced from said immortalized cells.

In another aspect the invention is a method of inducing active immunity to infection by *staphylococci* in a subject. The method includes the step of administering to a subject an effective amount for inducing active immunity to *staphylococci* of any of the above-described compositions.

In one embodiment the method is a method for inducing immunity to infection by *staphylococcus aureus*. In another embodiment the method is a method for inducing immunity to infection by *staphylococcus epidermis*.

According to another aspect of the invention a method of inducing passive immunity to infection by *staphylococcus aureus* in a subject is provided. The method includes the step of administering to a subject an effective amount for inducing opsonization of *staphylococcus aureus* of an anti-PS/A antibody. In some embodiments the anti-PS/A antibody is prepared using an antigen as described herein.

In another aspect of the invention another method for preparing a pure polysaccharide is provided. The method includes the step of preparing an acid or base solution by incubating a bacterial culture with a strong base or a strong acid. The acid or base solution is then neutralized to pH 7 to produce a crude antigen suspension. The crude antigen suspension is dialyzed against a solution such as deionized water and insoluble crude antigen can be collected. In some embodiments the insoluble crude antigen can be lyophilized and then resuspended in a buffer. In some embodiments the buffer is selected from the group consisting of 50 mM PBS and 100 mM Tris with 150 mM NaCl. In other embodiments the strong base or acid is greater than 1 M NaOH or HCL. In other embodiments the strong base or acid is 5 M NaOH or HCL. In another embodiment the bacterial culture extract is stirred in the strong base or acid for 18–24 hours. In yet another embodiment the strong base or acid extraction is repeated.

Another aspect of the invention describes a method of evaluating the ability of an antigen to protect against *staphylococci aureus* in a subject. The method involves administering to the subject an effective amount of the antigen, wherein the antigen induces active immunity recognizing an antigen described herein, including the embodiments. Exposing the subject to *staphylococci aureus* and testing for the presence of *staphylococci aureus* in the subject. Preferably the antigen induces active immunity against poly β 1-6-N-acetylglucosamine and is at least about 75% pure and/or less than 10% galactose is present in the preparation containing the antigen. In different embodiments the antigen is at least about 92%, 95%, or 97% pure and/or less than 5% or 1% galactose is present in the preparation containing the antigen. In another embodiment the invention features a method for inducing active immunity to *staphylococci* infection in a subject by administering one of the antigens identified by this method.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE SEQUENCES

Figure 1:
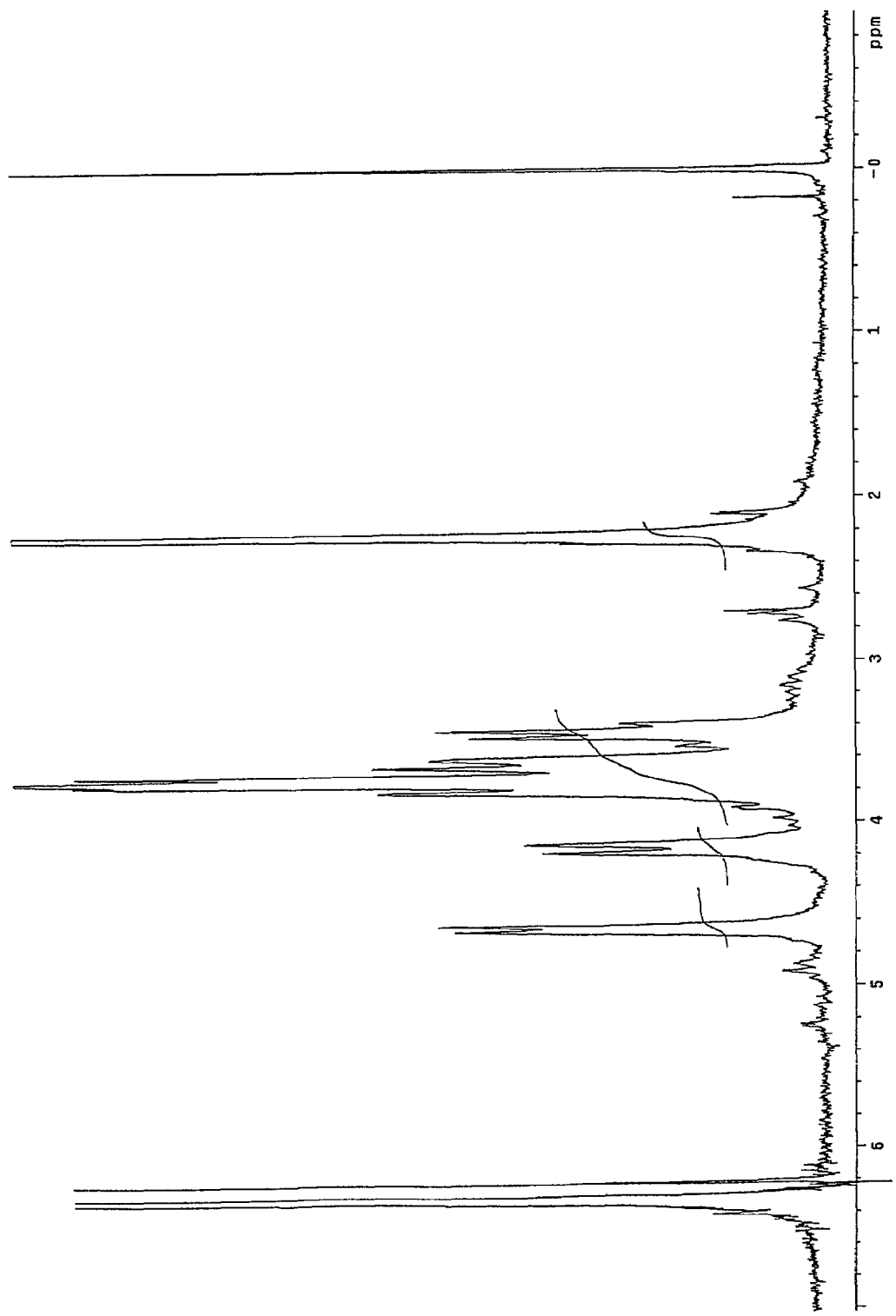
FIG. 1 is an NMR spectra of PS/A from *S. aureus* strain MN8.

SEQ. ID. NO. 1 is nucleic acid sequence of the ica locus which has been deposited in GenBank under accession number U43366. (Prior Art)

SEQ. ID. NO. 2 is a forward primer sequence for ica.

SEQ. ID. NO. 3 is a backward primer sequence for ica.

DETAILED DESCRIPTION OF THE INVENTION

The invention relates to a microcapsule from *Staphylococcal* bacteria which is useful for inducing immunity to bacterial infection and also for producing antibodies for diagnostic and therapeutic purposes. The microcapsule is a PS/A preparation which can be isolated from *Staphylococcus aureus* or coagulase-negative *staphylococci*, or can be synthesized de novo. PS/A has not previously been identified as being a component of the *Staphylococcus aureus* extracellular layer. Prior to the instant invention, it was demonstrated that two chemically related serologic types of capsule, termed capsular polysaccharide CP5 and CP8 were produced by 90% of *Staphylococcus aureus* strains. It was believed that these capsular polysaccharides were responsible for inducing immune recognition of *S. aureus*. It has been discovered according to the invention that *S. aureus* includes a true capsule which either extends out beyond or replaces the CP5 or CP8 layer and is responsible for provoking an immune response. As demonstrated in the examples presented herein, the PS/A antigen can produce opsonic protective antibodies against coagulase positive *staphylococci* such as *S. aureus* and coagulase-negative *staphylococci* when administered in vivo.

Prior to the invention, the inventor of the instant application identified and characterized a portion of the capsule of coagulase-negative *staphylococci*, which was PS/A (U.S. Pat. No. 5,055,455, issued to Gerald B. Pier). It was found that the PS/A of coagulase negative *staphylococcus* is a component of the cell surface and biofilm layer and is involved in protecting the bacterial cell from host defenses, such as opsonophagocytosis (Kojima, Y., M. Tojo, D. A. Goldmann, T. D. Tosteson and G. B. Pier. (1990) *J Infect Dis*. 162:435. Tojo, M., N. Yamashita, D. A. Goldmann and G. B. Pier. (1988) *J Infect Dis*. 157:713. Goldmann, D. A. and G. B. Pier. (1993) *Clin Microbiol Rev*. 6:176.) The chemical structure of the PS/A, however, was not identified because of the difficulty associated with purifying the isolated PS/A. It was only possible to achieve a preparation of approximately 90% purity. According to the methods of the instant invention, the PS/A antigen has been isolated and purified to achieve a pure PS/A preparation.

As used herein, a "pure PS/A preparation" is a PS/A preparation which has been isolated or synthesized and which is greater than 92% free of contaminants and/or is substantially free of galactose. In some embodiments the PS/A is greater than 93%, 94%, 95%, 96%, 97%, 98%, 99% or is 100% free of contaminants. A PS/A antigen substantially free of galactose indicates the presence of less than 10%, preferably less than 5%, or more preferably less than 1% galactose, from preparation containing the antigen. Preferably, the material is greater than 95% or even greater than 97% or 99% free of contaminants. The degree of purity of the PS/A antigen can be assessed by any means known in the art. For example, the purity can be assessed by chemical analysis assays as well as gas chromatography and nuclear magnetic resonance to verify structural aspects of the material. Although it is not preferred, it is possible that the PS/A is greater than 90 or 91% free of contaminants.

One major contaminant of some prior art PS/A antigen preparations was phosphate containing teichoic acid. The teichoic acid contamination of the prior art antigen interfered with both the chemical characterization and the immunogenicity of the antigen. The procedures used in the prior art to isolate PS/A were not sufficient to consistently remove contaminating teichoic acid from the PS/A preparation, making the chemical characterization of the PS/A antigen impossible. The methods of the invention described herein are consistently capable of producing an isolated PS/A antigen preparation which is substantially free of teichoic acid. A PS/A preparation that is substantially free of teichoic acid is one which has less than 1.0% phosphate. In some embodiments the PS/A preparation that is substantially free of teichoic acid is one which has less than 0.1% phosphate. The amount of phosphate present in the sample can be assessed by any means known in the art. As described in the examples below the amount of phosphate contamination can be assessed using the methods described in Keleti, G. and W. H. Lederer, ((1974) *Handbook of Micromethods for the Biological Sciences* Van Nostrand Reinhold Co., New York), which is hereby incorporated by reference. Briefly, the assay is performed as follows: to 100 μg of sample 100 μl of a solution made by adding together 43.5 ml of water, 6.5 ml of 70% perchloric acid ($HCLO_4$) and 50 ml of 20 N sulfuric acid ($H_2SO_4$) is added. This is heated at 95° C. for 2 hours in a tube with a marble on top of it. The mixture is next placed in an oven at 165° C. and heated for an additional 2 hours then cooled to room temperature. Next, one ml of reagent 5, made by the following method, is added to the sample:

Reagent 1: 1.36 grams of sodium acetate 0.3H$_2$0 dissolved in 10 ml water.

Reagent 2: 500 mg ammonium molybdate dissolved in 20 ml water.

Reagent 3: 2 ml of reagent 1, 2 ml of reagent 2 and 16 ml of water.

Reagent 4: 2 gm ascorbic acid dissolved in 20 ml water, prepared immediately prior to use.

Reagent 5: Add in an ice bath 9 ml of reagent 3 and 1 ml of reagent 4.

After adding reagent 5 the tubes are mixed thoroughly and the optical density read at 820 nanometers in a spectrophotometer. A standard curve consisting of sodium phosphate monobasic (range of 0.1–5 µg per tube) is used to calculate the amount of phosphate present in the test samples. (Lowry, O. H., N. R. Roberts, K. Y. Leiner, M. L. Wu and A. L. Farr., (1954), *Biol. Chem.* 207, 1.)

Thus, the invention encompasses pure PS/A antigens, compositions containing the antigens, vaccines containing the antigens and methods of using and making the antigens. In some aspects the PS/A antigens have the following structure:

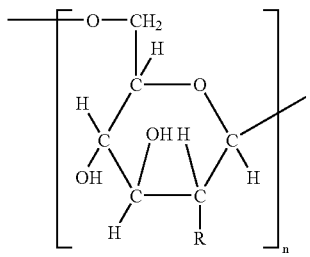

In the structure, n is an integer greater than or equal to 300, R is selected from the group consisting of —NH—CO—(CH$_2$)$_m$—COOH, —NH—CO—CH$_3$, and —NH$_2$, m being 1–5, and at least 50% of the R groups are —NH—CO—CH$_3$. Preferably the antigen has a molecular weight of at least 100,000 Daltons. The native PS/A material has a β 1-6 linkage. This is the preferred backbone linkage in the PS/A antigen of the invention.

In this aspect of the invention the PS/A antigen is a homopolymer of at least partially substituted glucosamine residues linked to one another. In other embodiments, the glucosamine residues can be substituted with 55%, 60%, 70%, 80%, 90%, 95%, 97%, or 100% of acetate. The substitution may be a homo-or hetero-substitution. A homo-substitution is one in which the glucosamine residues are substituted with a single type of substituent. For instance, the glucosamine residues may be substituted only with acetate residues. In the hetero-substitution, the glucosamine residues may be substituted with more than one type of substituent. For instance, some of the glucosamine residues may be substituted with succinic acid and others may be substituted with acetate. A composition of PS/A according to the invention includes all homo-substituted PS/A molecules or all hetero-substituted PS/A molecules or a combination thereof.

The invention according to another aspect includes synthetic PS/A which differs from the native antigen in the degree and type of substitution. Some preparations of native PS/A antigen are approximately 100% substituted with acetate (1 glucosamine: 1 acetate). It has been discovered according to the invention that the extent of acetylation varies depending on the growth conditions and strain of *staphylococcus* used to prepare the antigen. One type of PS/A antigen according to the invention includes an antigen in which between 50 and 95% of the glucosamine residues are substituted with acetate. The invention also includes PS/A antigens having between 50 and 100% substitution with a acetate or a mixture of a short chain fatty acid and acetate. In some embodiments the PS/A antigen has at least 55, 60, 65, 70, 75, 80, 85, 90, 95, or 97% acetate.

The native PS/A antigen is a high molecular weight homopolymer of greater than 100,000 Daltons. In some aspects the antigens of the invention, however, includes low molecular weight and high molecular weight homopolymers of substituted monomers. The size of the polysaccharides useful according to the invention varies greatly. Polysaccharides between 500 and 20,000,000 Daltons will be typical. The polysaccharides of smaller molecular weight may be conjugated to carriers when used as therapeutic or diagnostic agents or may be used alone. Preferably, the polysaccharide composition of the invention has a molecular weight of at least 10,000 Daltons and more preferably at least 30,000 Daltons, and in some aspects the minimum molecular weight of the antigen is 100,000 Daltons.

The value of n in the above structure has an impact on the molecular weight of the antigen. When n is equal to or greater than 300, then the molecular weight of the minimal polysaccharide in the structure is 60,918 Daltons (300 units×203 Daltons/unit+18 Daltons for the substituents on the terminal residues). If the antigen has a minimum molecular weight of 100,000 Daltons, then either the polysaccharide defined be the structure can have more than 300 units or the polysaccharide can be conjugated to a carrier compound which makes up for the difference in the molecular weight. If for instance the polysaccharide had 490 units or 500 units, the molecular weight of the polysaccharide is 99,488 or 101,518 Daltons respectively.

The native material includes glucosamine monomers linked together by a β-1-6 linkage. Some forms of the polysaccharide antigens of the invention, however, include monomers linked together by either an α- or a β-1-6, 1-4, or 1-3 linkage or a combination thereof. In a preferred embodiment the polysaccharide is linked together by a β1-6 linkage.

The compositions of the invention can be isolated from natural sources or synthesized. The invention includes methods for isolating and purifying PS/A antigen from *staphylococci*, as well as products prepared by those methods. One method of the invention involves incubating an impure PS/A with a base or acid to produce a semi-pure PS/A preparation, neutralizing the preparation, and treating the neutralized preparation to produce the pure PS/A.

The method is used to purify an impure PS/A preparation. An impure PS/A can be prepared by a variety of methods including extracting a crude PS/A preparation from a bacterial culture, including cells and cell free culture supernatants, isolating a high molecular weight PS/A-enriched material from the crude PS/A preparation, and precipitating an impure PS/A containing the high molecular weight PS/A-enriched material with a solvent such as methanol, ethanol, acetone or any other organic solvent known to one skilled in the art as being capable of causing the precipitation of polysaccharides from aqueous solutions. The steps of extracting the crude PS/A preparation and isolating and precipitating the impure PS/A antigen preparation are performed by any methods known in the art, such as those including U.S. Pat. No. 5,055,455. This impure material is then purified to produce the composition of the invention.

The purification steps are achieved by incubating the impure PS/A antigen with bacterial enzymes that can digest biological materials, including nuclease enzymes such as DNAase and RNAase to digest DNA and RNA, protease enzymes such as proteinase k to digest proteins, addition of a solvent that will precipitate the PS/A antigen out of solution, collection of the precipitate and redissolution of the PS/A in a base, such as NaOH or an acid such as HCL, followed by neutralization. The neutralization can be accomplished using a base if the incubation step was performed with an acid or with an acid if the incubation step was performed with a base. The insoluble fraction from the neutral material neutral material is then treated, e.g., by incubation in hydrofluoric acid to produce a pure PS/A antigen or by redissolution in buffers with a pH<4.0 followed by molecular sieve and/or ion-exchange chromatography to achieve the material of the invention.

Another method of the invention includes the steps of extracting a crude antigen suspension from a bacteria culture by incubating the bacteria with a strong base or acid. Preferably, the bacterial is stirred in the strong base or acid for at least 2 hours, and more preferably at least 5, 10, 15, 18 or 24 hours. The strong base or acid can be any type of strong base or acid, but is preferably greater than 1 Molar NaOH or HCL. In some embodiments the strong base or acid is 5 Molar NaOH or HCL. The acid or base solution is then subjected to centrifugation to collect the cell bodies. In some embodiments the extraction procedure is repeated several times. The resultant acid or base solution is neutralized to approximately pH 7 and then dialyzed to produce an insoluble impure crude antigen.

PS/A can be purified from any bacterial strains expressing the ica locus. These strains include, for example, but are not limited to *S. epidermis, S. aureus*, and other strains such as *S. carnosus* which have been transformed with the genes in the ica locus. In particular, pure PS/A has been isolated and purified from specific strains including *S. epidermis* RP62A (ATCC number: 35984), *S. epidermis* RP12 (ATCC number: 35983), *S. epidermis* M187, *S. carnosis* TM300 (pCN27), *S. aureus* RN4220 (pCN27), and *S. aureus* MN8 mucoid.

The PS/A useful according to the invention also may be synthesized from naturally occurring polysaccharides that do not possess the substituted monomeric unit of native PS/A. For instance, the PS/A antigen of the invention may be synthesized by chemically modifying a polymer of polyglucosamine-like monomeric residues such that those residues are substituted with acetate alone and/or with a short chain fatty acid. The resultant polysaccharide is a polymer of monomeric repeating units selected from the group consisting of β 1-6, α 1-6, α 1-4, α 1-3, β 1-4, and β 1-3 polyglucose having the substitution on the C2 atom of the polyglucose. For example, certain naturally occurring polysaccharides have repeating units of an imine group which can be reduced to form a free amino moiety, which can be derivitized, thereby creating the necessary structural motif. Other naturally occurring polysaccharides are naturally substituted with acetate but have backbones other than a β-1,6 structure. These types of polysaccharides ban be used in combination with polysaccharides having a β-1,6 structure.

Compounds which are useful for these synthetic reactions are known to those of skill in the art in view of the PS/A structure disclosed herein and include, but are not limited to, chitin, chitosan, polyglucose (i.e., dextran), polyglucosamine, and polyglucosaminouronic acid. Chitin for example is a poly-N-acetyl glucosamine with β-1-4 linkages, having the following structure:

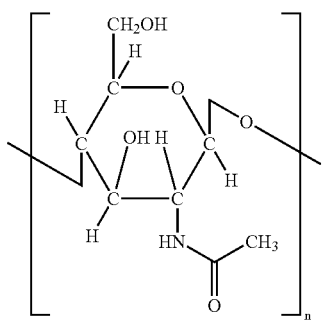

Chitosan, which is a polyglucosamine with β-1-4 linkages having the following structure:

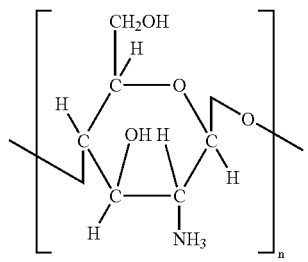

The free amino groups of this compound can be substituted with acetate, succinate or any other short chain fatty acid using procedures well known in the art. One not limiting example of a method is accomplished using the following procedure with the following reagents: 69 mM Sodium Borate, 10 NaOH, acetic or succinic anhydride and 12N HCl. The sample is suspended on 30 ml sodium borate buffer, and the pH is raised to >10 with 10N NaOH. 1.8 ml of acetic anhydride (or equivalent succinic anhydride) is added in 300 µl amounts and titrated with 10N NaOH to keep pH above 10. The mixture is then stirred for 2 hours maintaining pH, and pH is neutralized with 12N HCl. The solution is then dialyzed and concentrated using ultrafiltration, followed by lyophilization to obtain acetylated or succinylated antigen.

Dextran is a polyglucose molecule with α-1-6 linkages, having the following structure:

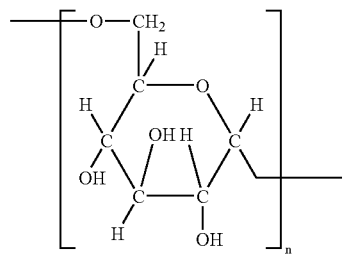

Polyglucosamines having various substituents which are encompassed by the PS/A antigen described, but which have lower molecular weights or which have different backbone structures may also be modified to produce the PS/A antigen of the invention. For instance polysaccharide intercellular adhesin (PIA) is a polymer of β-1-6 linked glucosamine residues substituted on the amine group with an acetate. PIA, polyglucosaminouronic acid, or polygalactosaminouronic acid may also be used to produce the large molecular weight PS/A antigen of the invention. PIA has the following structure:

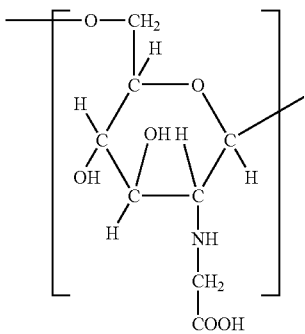

For instance the capsular polysaccharide (Vi antigen) of *Salmonella typhi* is formed entirely of repeating α-1-4 linked monomers of galactosaminuronic acid. This acid includes an N-acetyl moiety. The carboxyl group of the uronic acid may also be modified to a $CH_2OH$ group, which is easily accomplished with a water soluble carbodiimide (described in Example 2). The isolation and preparation of *Salmonella typhi* capsule Vi antigen is described in Szu, S. C., et al. (Relation between structure and immunologic properties of the Vi capsular polysaccharide, *Infection and Immunity.* 59:4555–4561 (1991)). The Vi antigen has the following structure:

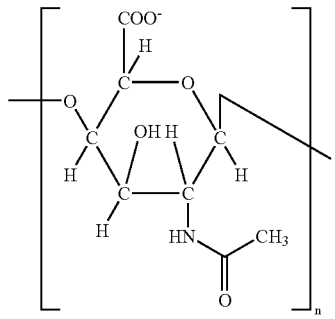

For those polysaccharides that contain imine moieties (C—NH), free amino groups can be formed by conventional chemistry techniques known to those of ordinary skill in the art. One suitable method involves the use of sodium borohydride. The imine group can be reduced with sodium borohydride to create a free amino group. This is done by adding in excess of 5 mg of borohydride to polysaccharide dissolved in distilled water while stirring at room temperature for 2 hours. The mixture is then dialyzed against water and freeze dried. DiFabio, J. L et al., *Id.*

The compositions of the invention are useful in a variety of different applications including in vitro, in situ and in vivo diagnosis of pathological status, such as infection. Additionally, these compositions may be used to immunize subjects in vivo to prevent or treat infection. The compositions may also be used to develop antibodies and other binding peptides which are useful for the same purposes as the PS/A compositions of the invention. Thus, the invention includes methods for generating antibodies which are specific for PS/A and which can be used in the diagnosis and treatment of infectious disorders.

The antibodies useful according to the invention may be either monoclonal antibodies or polyclonal antibodies. Polyclonal antibodies generally are raised in animals by multiple subcutaneous or intraperitoneal injections of an antigen and an adjuvant. Polyclonal antibodies to PS/A antigen can be generated by injecting the PS/A antigen alone or in combination with an adjuvant, or by injecting PS/A conjugated to a carrier compound. For instance, it may be useful to conjugate the PS/A antigen to a protein, e.g., keyhole limpet hemocyanin, serum albumin, bovine thyroglobulin, or soy bean trypsin inhibitor, or other compound that is immunogenic in the species of animal to be immunized.

A "carrier compound" as used herein is a compound which can be conjugated to a polysaccharide either directly or through the use of a linker and which may be immunologically active or inert. Carrier compounds include but are not limited to proteins or peptides, polysaccharides, nucleic acids or other polymers, lipids, and small molecules.

Many methods are known in the art for conjugating a polysaccharide to a protein. In general, the polysaccharide should be activated or otherwise rendered amenable to conjugation, i.e., at least one moiety must be rendered capable of covalently bonding to a protein or other molecule. Many such methods are known in the art. For instance, U.S. Pat. No. 4,356,170, issued to Jennings, describes the use of periodic acid to generate aldehyde groups on the polysaccharide and then performs reductive amination using cyanoborohydride. U.S. Pat. No. 4,663,160, issued to Tsay et al., also used periodic acid to generate aldehyde groups but then linked the polysaccharide to a protein derivatized with a 4–12 carbon moiety (prepared in the presence of a condensing agent) with a Schiff's base reaction in the presence of a reducing agent such as cyanoborohydride. U.S. Pat. No. 4,619,828, issued to Gordon, used cyanogen bromide to active the polysaccharide and then conjugated it through a spacer bridge of 4–8 carbon atoms to the protein. In U.S. Pat. No. 4,808,700, issued to Anderson and Clements, a polysaccharide was modified to produce at least one reducing end using limited oxidative cleavage by periodate, hydrolysis by glycosidases, or acid hydrolysis and was conjugated to a protein through reductive amination in the presence of cyanoborohydride. U.S. Pat. No. 4,711,779, issued to Porro and Costantino, described the activation of polysaccharides by introducing primary amino groups into the terminal reducing group using sodium cyanoborohydride, followed by conversion to esters in the presence of adipic acid derivatives and conjugation to a toxoid in the presence of an organic solvent, such as dimethylsulfoxide. Many other methods of conjugation are known in the art.

The carrier compound may be directly linked to the PS/A antigen or may be connected to the PS/A antigen through a linker or spacer. A polysaccharide may be coupled to a linker or a spacer by any means known in the art, for example, using a free reducing end of the polysaccharide to produce a covalent bond with a spacer or linker. A covalent bond may be produced by converting a free reducing end of a PS/A antigen into a free 1-aminoglycocide, which can subsequently be covalently linked to a spacer by acylation. (Lundquist et al., *J. Carbohydrate Chem.*, 10:377 (1991)). Alternatively, the PS/A antigen may be covalently linked to the spacer using an N-hydroxysuccinimide active ester as activated group on the spacer. (Kochetkow, *Carbohydrate*

Research, 146:C1 (1986)). The free reducing end of the PS/A antigen may also be converted to a lactone using iodine and potassium hydroxide. (Isebell et al., *Methods of Carbohydrate Chemistry*, Academic Press, New York (1962)). The lactone can be covalently linked to the spacer by means of a primary amino group on the spacer or linker. The free reducing end of the PS/A antigen may also be covalently linked to the linker or spacer using reductive amination.

The carrier compound linked to the PS/A antigen may be an immunologically active or inert protein. Proteins include, for example, plasma proteins such as serum albumin, immunoglobulins, apolipoproteins and transferrin, bacterial polypeptides such as TRPLE, β-galactosidase, polypeptides such as herpes gD protein, allergins, diphtheria and tetanus toxoids, salmonella flagellin, hemophilus pilin, hemophilus 15 kDa, 28–30 kDa, and 40 kDa membrane proteins, escherichia coli, heat label enterotoxin ltb, cholera toxin, and viral proteins including rotavirus VP and respiratory syncytial virus f and g proteins. The proteins which are useful according to the invention include any protein which is safe for administration to mammals and which serves as an immunologically effective carrier protein.

To prepare the polyclonal antibodies the PS/A antigen or antigen conjugate generally is combined with an adjuvant such as Freund's complete adjuvant or other adjuvant (100 μg of conjugate for rabbits or mice in 3 volumes of Freund's) and injected intradermally at multiple sites. Approximately one month later, the animals are boosted with $\frac{1}{5}$–$\frac{1}{10}$ of the original amount of antigen or antigen conjugate in adjuvant by subcutaneous injection at multiple sites. One to two weeks later the animals are bled, and the serum is assayed for the presence of antibody. The animals may be repeatedly boosted until the antibody titer plateaus. The animal may be boosted with the PS/A antigen alone, the PS/A antigen conjugate, or PS/A conjugated to a different carrier compound with or without an adjuvant.

In addition to supplying a source of polyclonal antibodies, the immunized animals can be used to generate PS/A antigen specific monoclonal antibodies. As used herein the term "monoclonal antibody" refers to a homogenous population of immunoglobulins which specifically bind to an epitope (i.e. antigenic determinant) of PS/A. Monoclonal antibodies can be prepared by any method known in the art such as by immortalizing spleen cells isolated from the immunized animal by e.g., fusion with myeloma cells or by Epstein-bar-virus transformation and screening for clones expressing the desired antibody. Other methods involve isolation of polyclonal antibodies and generating monoclonal antibodies using immortalized cell lines. Methods for preparing and using monoclonal antibodies are well known in the art.

Murine anti-PS/A monoclonal antibodies may be made by any of these methods utilizing PS/A as an immunogen. The following description of a method for developing an anti-PS/A monoclonal antibody is exemplary and is provided for illustrative purposes only. Balb/c mice are immunized intraperitoneally with approximately 75–100 μg of purified PS/A in an complete Freund's adjuvant. Booster injections of approximately 25–50 μg PS/A in incomplete Freund's are administered on approximately days 15 and 35 after the initial injection. On day 60–65, the mice receive booster injections of approximately 25 μg PS/A in the absence of adjuvant. Three days later, the mice are killed and the isolated spleen cells fused to murine myeloma NS-1 cells using polyethylene glycol by a procedure such as that described by Oi (Oi VT: Immunoglobulin-producing hybrid cell lines in *Hezenberg LA* (ed): selected methods in cellular biology, San Francisco, Calif., Freeman, (1980)). Hybridoma cells are selected using hypoxanthine, aminopterin, and thymidine (HAT) and grown in culture. Fourteen to fifteen days after fusion, hybridoma cells producing anti-PS/A monoclonal antibodies are identified using a solid-phase radioimmunoassay by capturing anti-PS/A antibodies from conditioned media with immobilized goat anti-mouse IgG followed by quantitation of specifically bound $^{125}$I-labeled PS/A. Hybridomas testing positive for antibodies against PS/A are subcloned by limiting dilution and retested. Ascites for the hybridomas is then prepared in pristane-primed BALB/c mice by injecting approximately $1 \times 10^6$ cells/mouse. Concentrates enriched in the selected monoclonal antibodies are produced from ascites fluid by gel filtration on S-200 and concentrated with $(NH_4)SO_4$. The pellets are dissolved in an appropriate storage solution such as 50% glycerol/$H_2O$ and are stored at 4° C.

An "anti-PS/A antibody" as used herein includes humanized antibodies and antibody fragments as well as intact monoclonal and polyclonal antibodies.

In preferred embodiments, the anti-PS/A antibody useful according to the methods of the invention is an intact humanized anti-PS/A monoclonal antibody in an isolated form or in a pharmaceutical preparation. A "humanized monoclonal antibody" as used herein is a human monoclonal antibody or functionally active fragment thereof having human constant regions and a PS/A binding region from a mammal of a species other than a human.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51–63 (Marcel Dekker, Inc, new York, 1987), and Boerner et al., *J. Immunol.*, 147: 86–95 (1991). In addition to the conventional methods for preparing human monoclonal antibodies, such antibodies may also be prepared by immunizing transgenic animals that are capable of producing human antibodies (e.g., Jakobovits et al., *PNAS USA*, 90:2551 (1993), Jakobovits et al., *Nature*, 362:255–258 (1993), Bruggermann et al., *Year in Immuno.*, 7:33 (1993) and U.S. Pat. No. 5,569,825 issued to Lonberg).

The following examples of methods for preparing humanized monoclonal antibodies that interact with PS/A are exemplary and are provided for illustrative purposes only. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Humanized antibodies have particular clinical utility in that they specifically recognize PS/A but will not evoke an immune response in humans against the antibody itself. In a most preferred embodiment, a murine CDR is grafted into the framework region of a human antibody to prepare the "humanized antibody." See, e.g., L. Riechmann et al., Nature 332, 323 (1988); M. S. Neuberger et al., Nature 314, 268 (1985) and EPA 0 239 400 (published Sep. 30, 1987).

Human antibodies may also be obtained by recovering antibody-producing lymphocytes from the blood or other tissues of humans producing antibody to PS/A. These lymphocytes can be treated with various types of DNA to produce cells that grow on their own in the laboratory under appropriate culture conditions. The cell cultures can be screened for those making antibody to PS/A, such cultures subjected to cloning to achieve cultures starting from a single cell, the these cloned cultures screened again to identify those producing PS/A. Such cultures themselves could be used to produce human monoclonal antibodies to PS/A or the genetic elements encoding the variable portions of the heavy and light chain of the antibody can be cloned and inserted into genetic vectors for production of antibody of different types.

PS/A binding antibody fragments are also encompassed by the invention. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)]. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316–325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644–646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15:1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the PS/A epitope.

The antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

Antibody fragments and other PS/A binding polypeptides having binding specificity for PS/A for the diagnostic methods of the invention as described herein also are embraced by the invention. Several routine assays may be used to easily identify such peptides. Screening assays for identifying peptides of the invention are performed for example, using phage display procedures such as those described in Hart, et al., *J. Biol. Chem.* 269:12468 (1994). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to PS/A are obtained by selecting those phages which express on their surface a ligand that binds to PS/A. These phages then are subjected to several cycles of reselection to identify the peptide ligandexpressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to PS/A. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to PS/A any known binding assay may be employed. For example, the peptide may be immobilized on a surface and then contacted with a labeled PS/A. The amount of PS/A which interacts with the peptide or the amount which does not bind to the peptide may then be quantitated to determine whether the peptide binds to PS/A. A surface having an anti-PS/A antibody immobilized thereto may serve as a positive control.

The compositions of the invention are useful for many in vivo, and in vitro purposes. For example, the compositions of the invention are useful for producing an antibody response, e.g., as a vaccine for active immunization of humans and animals to prevent *S. aureus* infection and infections caused by other species of bacteria that make the PS/A antigen; as a vaccine for immunization of humans or animals to produce anti-PS/A antibodies that can be administered to other humans or animals to prevent or treat *staphylococcal* infections; as an antigen to screen for important biological agents such as monoclonal antibodies capable of preventing *S. aureus* infection, libraries of genes involved in making antibodies, or peptide mimetics; as a diagnostic reagent for *S. aureus* infections and infections caused by other species of bacteria that make the PS/A antigen; and as a diagnostic reagent for determining the immunologic status of humans or animals in regard to their susceptibility to *S. aureus* infections and infections caused by other species of bacteria that make the PS/A antigen.

The PS/A of the invention can be used to protect a subject against infection with a bacteria which has a PS/A capsule on its surface by inducing active immunity to infection by *staphylococci* in a subject. The method is accomplished by administering to the subject an effective amount for inducing an immune response against a *staphylococci* of any of the PS/A compositions of the invention described above. This process is also referred to as active immunity.

"Active immunity" as used herein involves the introduction of an antigen into a subject such that the antigen causes differentiation of some lymphoid cells into cells that produce antibody and in certain instances other lymphoid cells into memory cell. The memory cells do not secrete antibodies but rather incorporate the antibodies into their membrane in order to sense antigen if it is administered to the body again.

The method is useful for inducing immunity to infection by *staphylococci*. "*Staphylococci*" as used herein refers to all *staphylococcal* bacterial species expressing a PS/A containing capsule. Bacteria which are classified as *staphylococci* are well known to those of skill in the art and are described in the microbiology literature. *Staphylococci* expressing a PS/A containing capsule include but are not limited *Staphylococcus epidermidis* (including RP62A (ATCC Number: 35984), RP12 (ATCC Number: 35983), and M187), *Staphylococcus aureus* (including RN4220 (pCN27) and MN8 mucoid), and strains such as *Staphylococcus carnosus* transformed with the genes in the ica locus (including TM300 (pCN27)). Other bacterial strains expressing a PS/A containing capsule can easily be identified by those of skill in the art. For instance a *staphylococcal* bacteria which expresses the ica locus will express a PS/A containing capsule. One of ordinary skill in the art can easily screen for the expression of mRNA or protein related of the ica locus since the nucleic acid sequence of the ica locus is known (SEQ ID NO. 1 and originally described in Heilmann, C., O. Schweitzer, C. Gerke, N. Vanittanakom, D. Mack and F. Gotz (1996) Molecular basis of intercellular adhesion in the biofilm-forming *Staphylococcus epidermidis. Molec. Microbiol.* 20:1083.) Although the Heilmann publication describes the nucleic acid sequence of the ica locus, the publication states but did not directly show that this locus encodes production of the PIA antigen. It was discovered according to the instant invention that ica also encodes for proteins involved in the production of PS/A. Bacterial strains expressing a PS/A containing capsule also can be identified by immunoelectron microscopy (or other immunoassay) using anti-PS/A antibodies to detect the presence of the capsule on the surface of the bacteria as described in Example 6 below. Additionally the capsule of bacterial strains can be isolated as described in Example 1 and analyzed using liquid chromatography and mass spectroscopy as described in Example 4 below.

A "subject" as used herein is a warm-blooded mammal and includes, for instance, humans, primates, horses, cows, swine, goats, sheep, chicken, dogs, and cats. In some embodiments the subject is a non-rodent subject. A non-rodent subject is any subject as defined above, but specifically excluding rodents such as mice, rats, and rabbits.

The PS/A of the invention may be administered to any subject capable of inducing an immune response to an antigen but are especially adapted to induce active immunization against systemic infection caused by *staphylococci* in a subject capable of producing an immune response and at risk of developing a *staphylococcal* infection. A subject capable of producing an immune response and at risk of developing a *staphylococcal* infection is a mammal possessing an immune system that is at risk of being exposed to environmental *staphylococci*. For instance, hospitalized patients are at risk of developing *staphylococcal* infection as a result of exposure to the bacteria in the hospital environment. In particular high risk populations for developing infection by *S. aureus* include, for example, renal disease patients on dialysis, and individuals undergoing high risk surgery. High risk populations for developing infection by *S. epidermidis* include, for example, patients with indwelling medical devices because clinical isolates are often highly adherent to plastic surfaces as a result of their extracellular material referred to as biofilm or slime. In some embodiments the subject is a subject that has received a medical device implant and in other embodiments the subject is one that has not received a medical device implant.

The PS/A of the invention is administered to the subject in an effective amount for inducing an antibody response. An "effective amount for inducing an antibody response" as used herein is an amount of PS/A which is sufficient to (i) assist the subject in producing its own immune protection by e.g. inducing the production of anti-PS/A antibodies in the subject, inducing the production of memory cells, and possibly a cytotoxic lymphocyte reaction etc. and/or (ii) prevent infection by *staphylococci* from occurring in a subject which is exposed to *staphylococci*.

An effective amount of a PS/A vaccine for stimulating an immune response as used herein is an amount of PS/A vaccine that is capable of eliciting the production of antibodies that are cross-reactive with at least two species of *staphylococcus*, e.g., *S. aureus* and *S. epidermidis*.

One of ordinary skill in the art can assess whether an amount of PS/A is sufficient to induce active immunity by routine methods known in the art. For instance the ability of a specific antigen to produce antibody in a mammal can be assessed by screening for antibodies in a mouse or other subject using the PS/A antigen.

A preferred method of the invention is a method for inducing active immunity to infection specifically by *Staphylococcus aureus* in a subject. Prior to the instant invention it was not known that *Staphylococcus aureus* expresses PS/A on its surface. It was believed that CP5 and CP8 made up the external capsule of *Staphylococcus aureus* and that these capsules might be effective antigens for inducing immunity. It was discovered according to the invention, however, that PS/A is useful as an antigen in inducing active immunity to infection by *Staphylococcus aureus*. The invention therefore includes the method of inducing immunity by administering to a subject a PS/A antigen.

The anti-PS/A antibodies of the invention are useful for inducing passive immunization in a subject by preventing the development of systemic infection in those subjects at risk of exposure to infectious agents. The method for inducing passive immunity to infection by *Staphylococcus aureus* is performed by administering to a subject an effective amount of an anti-PS/A antibody for inducing opsonization of *Staphylococcus aureus*.

"Passive immunity" as used herein involves the administration of antibodies to a subject, wherein the antibodies are produced in a different subject (including subjects of the same and different species), such that the antibodies attach to the surface of the bacteria and cause the bacteria to be phagocytized.

The anti-PS/A antibody of the invention may be administered to any subject at risk of developing a *staphylococcal* infection to induce passive immunity. The anti-PS/A antibody can even be administered to a subject that is incapable of inducing an immune response to an antigen. Although vaccination with a PS/A antigen might not be effective in high risk immunocompromised subjects, these subjects will benefit from treatment with antibody preparations raised against *Staphylococcus aureus*. A subject that is incapable of inducing an immune response is an immunocompromised subject (e.g. patient undergoing chemotherapy, AIDS patient, etc.) or a subject that has not yet developed an immune system (e.g. preterm neonate). The anti-PS/A antibody may be administered to a subject at risk of developing a *staphylococcal* infection to prevent the infectious agent from multiplying in the body or to kill the infectious agent. The anti-PS/A antibody may also be administered to a subject who already has an infection caused by *staphylococci* to prevent the infectious agent from multiplying in the body or to kill the infectious agent.

The anti-PS/A antibody of the invention is administered to the subject in an effective amount for inducing an immune response to *Staphylococcus aureus*. An "effective amount for inducing an immune response to *Staphylococcus aureus*" as used herein is an amount of PS/A which is sufficient to (i) prevent infection by *staphylococci* from occurring in a subject which is exposed to *staphylococci*; (ii) inhibit the development of infection, i.e., arresting or slowing its development; and/or (iii) relieve the infection, i.e. eradication of the bacteria causing the infection.

Using routine procedures known to those of ordinary skill in the art, one can determine whether an amount of anti-PS/A antibody is an "effective amount for inducing an immune response to *Staphylococcus aureus*" in an in vitro opsonization assay which is predictive of the degree of opsonization of an antibody. An antibody which opsonizes a *staphylococcal* bacteria is one which when added to a sample of *staphylococcal* bacteria causes phagocytosis of the bacteria. An opsonization assay may be a colorimetric assay, a chemiluminescent assay, a fluorescent or radiolabel uptake assay, a cell mediated bactericidal assay or other assay which measures the opsonic potential of a material. For instance, the following opsonization assay may be used to determine an effective amount of anti-PS/A antibody. The anti-PS/A antibody is incubated with an *staphylococcal* bacteria and a eukaryotic phagocytic cell and optionally complement proteins. The opsonic ability of the anti-PS/A antibody is determined based on the amount of *staphylococci* that remain after incubation. This can be accomplished by comparing the number of surviving *staphylococci* between two similar assays, only one of which includes opsonizing immunoglobulin or by measuring the number of viable *staphylococci* before and after the assay. A reduction in the number of *staphylococci* indicates opsonization.

The methods of the invention are also useful for inducing passive immunization to coagulase negative *staphylococci* in a subject by administering to a subject an effective amount for inducing opsonization of coagulase negative *staphylococci* of an anti-PS/A$_{pure}$ antibody. Although antibodies directed to PS/A isolated from coagulase negative *staphylococci* have been developed in the prior art and used to induce passive immunity to coagulase negative *staphylococci*, anti-PS/A$_{pure}$ antibodies have not previously been used for this purpose. An, anti-PS/A$_{pure}$ antibody as used herein is an antibody which specifically interacts with a pure PS/A antigen of the invention and induces opsonization of coagulase negative *staphylococci* but which does not interact with the impure preparation of PS/A of the prior art. As discussed above the impure PS/A preparation of the prior art was contaminated with teichoic acid or other impurities which interfered with the immunogenicity of the antigen. One of ordinary skill in the art can easily identify whether an anti-PS/A antibody is an anti-PS/A$_{pure}$ antibody by using routine biding assays. For instance, an anti-PS/A antibody may be immobilized on a surface and then contacted with a labeled impure PS/A preparation or a labeled pure PS/A preparation. The amount of PS/A preparation (pure vs. impure preparation) which interacts with the antibody or the amount which does not bind to the antibody may then be quantitated to determine whether the antibody binds to an impure PS/A preparation.

Subjects having a high risk of developing infection by *S. epidermidis* include, for example, preterm neonates, patients undergoing chemotherapy, and other patients with indwelling medical devices. Clinical isolates are often highly adherent to plastic surfaces because they elaborate an extracellular material referred to as biofilm or slime.

When PS/A antigen is used to prevent bacterial infection, it is formulated as a vaccine. A suitable carrier media for formulating a vaccine includes sodium phosphate-buffered saline (pH 7.4) or 0.125 M aluminum phosphate gel suspended in sodium phosphate-buffered saline at pH 6 and other conventional media. Generally, vaccines contain from about 5 to about 100 μg, preferably about 10–50 μg of antigen are suitable to elicit effective levels of antibody against the PS/A antigen in warm-blooded mammals. When administered as a vaccine the PS/A can optionally include an adjuvant.

The term "adjuvant" is intended to include any substance which is incorporated into or administered simultaneously with the PS/A of the invention which potentiates the immune response in the subject. Adjuvants include but are not limited to aluminum compounds, e.g., gels, aluminum hydroxide and aluminum phosphate, and Freund's complete or incomplete adjuvant (e.g., in which the PS/A antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide. Rare earth salts, e.g., lanthanum and cerium, may also be used as adjuvants. The amount of adjuvants depends on the subject and the particular PS/A antigen used and can be readily determined by one skilled in the art without undue experimentation.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, ptoluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% W/V).

The present invention provides pharmaceutical compositions, for medical use, which comprise PS/A of the invention together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the PS/A antigens of the present invention, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The preparations of the invention are administered in effective amounts. An effective amount, as discussed above, is that amount of a PS/A antigen or anti-PS/A antibody that will alone, or together with further doses, induce active immunity or opsonization of the infectious bacteria, respectively. It is believed that doses ranging from 1 nanogram/ kilogram to 100 milligrams/kilogram, depending upon the mode of administration, will be effective. The preferred range is believed to be between 500 nanograms and 500 micrograms/kilogram, and most preferably between 1 microgram and 100 micrograms/kilograms. The absolute amount will depend upon a variety of factors including whether the administration is performed on a high risk subject not yet infected with the bacteria or on a subject already having an infection, the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the pharmaceutical compositions of the invention are contemplated. Generally immunization schemes involve the administration of a high dose of an antigen followed by subsequent lower doses of antigen after a waiting period of several weeks. Further doses may be administered as well. The dosage schedule for passive immunization would be quite different with more frequent administration if necessary. Any regimen that results in an enhanced immune response to bacterial infection and/or subsequent protection from infection may be used. Desired time intervals for delivery of multiple doses of a particular PS/A can be determined by one of ordinary skill in the art employing no more than routine experimentation.

A variety of administration routes are available. The particular mode selected will depend, of course, upon the particular PS/A selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous injections, intravenous, intramuscular, intraperitoneal, intra sternal injection or infusion techniques. Other routes include but are not limited to oral, nasal, dermal, sublingual, and local.

The compositions may conveniently be presented in unit dosage form and may be prepared by any of the methods well known in the art of pharmacy. All methods include the step of bringing the active PS/A into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the polysaccharides of the invention, increasing convenience to the subject and the physician. Many types of release delivery systems are available and known to those of ordinary skill in the art. They include polymer based systems such as polylactic and polyglycolic acid, polyanhydrides and polycaprolactone; non-polymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. No. 4,748,034 and U.S. Pat. No. 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

It will also be appreciated by those of ordinary skill in the art that the PS/A antigens of the present invention have adjuvant properties by themselves. To the extent that the polysaccharides described herein potentiate human immune responses, they can be used as adjuvants in combination with other materials.

The PS/A antigens and anti-PS/A antibodies of the invention may be delivered in conjunction with another anti-bacterial antibiotic drug or in the form of anti-bacterial, antibiotic cocktails or with other bacterial antigens or antibodies. An anti-bacterial antibiotic cocktail is a mixture of any of a composition useful according to this invention with an anti-bacterial antibiotic drug. The use of antibiotics in the treatment of bacterial infection is routine. The use of antigens for inducing active immunization and antibodies to induce passive immunization is also routine. In this embodiment, a common administration vehicle (e.g., tablet, implant, injectable solution, etc.) could contain both the composition useful in this invention and the anti-bacterial antibiotic drug and/or antigen/antibody. Alternatively, the anti-bacterial antibiotic drug and/or antigen/antibody can be separately dosed.

Anti-bacterial antibiotic drugs are well known and include: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxime, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's, Pharmacological Basics of Therapeutics, 8th Ed., 1993, McGraw Hill Inc.)

Other polysaccharide antigens and antibodies are well known in the art. For instance, the following polysaccharide antigens and/or antibodies thereto can be administered in conjunction with the PS/A antigen and/or antibody: PIA, *Salmonella typhi* capsule Vi antigen (Szu, S. C., X. Li, A. L. Stone and J. B. Robbins, Relation between structure and immunologic properties of the Vi capsular polysaccharide, *Infection and Immunity.* 59:4555–4561 (1991)); *E. Coli* K5 capsule (Vann, W., M. A. Schmidt, B. Jann and K. Jann, The structure of the capsular polysaccharide (K5 antigen) of urinary tract infective *Escherichia coli,* 010:K5:H4. A polymer similar to desulfoheparin, *European Journal of Biochemistry.* 116:359–364, (1981)); *Staphylococcus aureus* type 5 capsule (Fournier, J. -M., K. Hannon, M. Moreau, W. W. Karakawa and W. F. Vann, Isolation of type 5 capsular polysaccharide from *Staphylococcus aureus, Ann. Inst. Pasteur/Microbiol.* (Paris). 138:561–567, (1987)); *Rhizobium melilori* expolysaccharide II (Glazebrook, J. and G. C. Walker, a novel expolysaccharide can function in place of the calcofluor-binding exopolysaccharide in nodulation of alfalfa by *Rhizobium meliloti, Cell.* 65:661–672 (1989)); *Group B streptococcus* type III (Wessels, M. R., V. Pozsgay, D. L. Kasper and H. J. Jennings, Structure and immunochemistry of an oligosaccharide repeating unit of the capsular polysaccharide of type III *group B Streptococcus, Journal of Biological Chemistry.* 262:8262–8267 (1987)); *Pseudomonas aeruginosa* Fisher 7O-specific side-chain (Knirel, Y. A., N. A. Paramonov, E. V. Vinogradov, A. S. Shashkow, B. A. N. K. Kochetkov, E. S. Stanislavsky and E. V. Kholodkova, Somatic antigens of *Pseudomonas aeruginosa* The structure of O-specific polysaccharide chains of lipopolysaccharides of *P. aeruginosa* O3(Lanyi), 025 (Wokatsch) and Fisher immunotypes 3 and 7, *European Journal of Biochemistry.* 167:549, (1987)); *Shigella sonnei* O-specific side chain (Kenne, L., B. Lindberg and K. Petersson, Structural studies of the O-specific side-chains of the *Shigella sonnei* phase I lipopolysaccharide, *Carbohydrate Research.* 78:119–126, (1980)); *S. pneumoniae* type I capsule (Lindberg, B., Lindqvist, B., Lonngren, J., Powell, D. A., Structural studies of the capsular polysaccharide from *Streptococcus pneumoniae* type 1, *Carbohydrate Research.* 78:111–117 (1980)); and *Streptococcus pneumoniae* group antigen (Jennings, H. J., C. Lugowski and N. M. Young, Structure of the complex polysaccharide C-substance from *Streptococcus pneumoniae* type 1, *Biochemistry.* 19:4712–4719 (1980)).

Other non-polypeptide antigens and antibodies thereto are well known to the those of skill in the art and can be used in conjunction with the PS/A compositions of the invention.

The PS/A antigens and antibodies are also useful in diagnostic assays for determining an immunologic status of a subject or sample or can be used as reagents in immunoassays. For instance, the antibodies may be used to detect the presence in a sample of a bacteria having a PS/A antigen on the surface. If the bacteria is present in the sample, then the antibodies may be used to treat the infected subject. The antibodies may also be used to screen bacteria for the presence of PS/A antigen and to isolate PS/A antigen and bacteria containing PS/A antigen from complex mixtures.

The above-described assays and any other assay known in the art can be accomplished by labeling the PS/A or antibodies and/or immobilizing the PS/A or antibodies on an insoluble matrix. The analytical and diagnostic methods for using PS/A and/or its antibodies use at least one of the following reagents: labeled analyte analogue, immobilized analyte analogue, labeled binding partner, immobilized binding partner, and steric conjugates. The label used can be any detectable functionality that does not interfere with the binding of analyte and its binding partner. Numerous labels are known for such use in immunoassays. For example, compounds that may be detected directly, such as fluorochrome, chemiluminescent, and radioactive labels, as well as compounds that can be detected through reaction or derivitization, such as enzymes. Examples of these types of labels include $^{32}$P, $^{14}$C, $^{125}$I, $^{3}$H, and $^{131}$I radioisotopes, fluorophores such as rare earth chelates or fluorescein and its derivatives, rhodamine and its derivatives, dansyl, umbelliferone, luciferases, such as firefly luciferase and bacterial luciferase (U.S. Pat. No. 4,737,456), luciferin, 2,3-dihydrophthalavinediones, horseradish peroxidase (HRP), alkaline phosphatase, β-galactosidase, glucoamylase, lysozyme, saccharide oxidases, such as glucose oxidase, galactose oxidase, and glucose-6-phosphate dehydrogenase. Heterocyclic oxidases such as uricase and xanthine oxidase, coupled to an enzyme that uses hydrogen peroxide to oxidize a dye precursor such as HRP, lactoperoxidase, or microperoxidase, biotin avidin, spin labels, bacteriophage labels, and stable free radicals.

The labels can be conjugated to the PS/A or antibody by methods known to those of ordinary skill in the art. For example, U.S. Pat. Nos. 3,940,475 and 3,645,090 demonstrate conjugation of fluorophores and enzymes to antibodies. Other assays which reportedly are commonly used with antigen and antibody and which can be used according to the invention include competition and sandwich assays.

The prior art has described several genes encoding proteins which contribute to the production of a polysaccharide, known as the polysaccharide intracellular adhesin (PIA). These genes have been cloned and expressed in other species of *staphylococcus*. It has been discovered according to the invention, however, that these genes also encode the production of proteins which cause the development of PS/A and in addition to PIA. Thus the invention includes a method of preparing PS/A antigen by producing a PS/A expressing host cell and isolating PS/A antigen.

A PS/A host cell can be prepared by transfecting or transforming a cell with the nucleic acid encoding the ica gene (SEQ ID NO: 1 or SEQ ID NO: 4). The cell can be a eukaryotic or prokaryotic cell but preferably is a bacterial cell. More preferably the cell is a *staphylococci* which does not ordinarily express PS/A.

The ica nucleic acid, in one embodiment, is operably linked to a gene expression sequence which directs the expression of the ica nucleic acid within a eukaryotic or prokaryotic cell. The "gene expression sequence" is any regulatory nucleotide sequence, such as a promoter sequence or promoter-enhancer combination, which facilitates the efficient transcription and translation of the ica nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and β-actin. Exemplary viral promoters which function constitutively in cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5'non-transcribing and 5'non-translating sequences involved with the initiation of transcription and translation, respectively. Such 5'non-transcribing sequences will include a promoter region which includes a promoter sequence for transcriptional control of the operably joined ica nucleic acid. The gene expression sequences optionally include enhancer sequences or upstream activator sequences as desired.

The ica nucleic acid sequence and the gene expression sequence are said to be "operably linked" when they are covalently linked in such a way as to place the transcription and/or translation of the ica coding sequence under the influence or control of the gene expression sequence. If it is desired that the ica sequence be translated into a functional protein, two DNA sequences are said to be operably linked if induction of a promoter in the 5' gene expression sequence results in the transcription of the ica sequence and if the nature of the linkage between the two DNA sequences does not (1) result in the introduction of a frame-shift mutation, (2) interfere with the ability of the promoter region to direct the transcription of the ica sequence, or (3) interfere with the ability of the corresponding RNA transcript to be translated into a protein. Thus, a gene expression sequence would be operably linked to a ica nucleic acid sequence if the gene expression sequence were capable of effecting transcription of that ica nucleic acid sequence such that the resulting transcript might be translated into the desired protein or polypeptide.

The ica nucleic acid of the invention can be delivered to the host cell alone or in association with a vector. In its broadest sense, a "vector" is any vehicle capable of facilitating: (1) delivery of a nucleic acid molecule containing the genes in the ica locus that encode production of proteins that synthesize the PS/A molecule or (2) uptake of a nucleic acid molecule containing the genes in the ica locus that encode production of proteins that synthesize the PS/A molecule by a target cell. Preferably, the vectors transport the ica molecule into the target cell with reduced degradation relative to the extent of degradation that would result in the absence of the vector. In general, the vectors useful in the invention are divided into two classes: biological vectors and chemical/physical vectors. Biological vectors are useful for delivery/uptake of ica nucleic acids to/by a target cell. Chemical/ physical vectors are useful for delivery/uptake of ica nucleic acids or ica polypeptides to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retroviruses, such as: Moloney murine leukemia virus; Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In addition to the biological vectors, chemical/physical vectors may be used to deliver a ica molecule to a target cell and facilitate uptake thereby. As used herein, a "chemical/physical vector" refers to a natural or synthetic molecule, other than those derived from bacteriological or viral sources, capable of delivering the ica molecule to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0 µm can encapsulate large macromolecules. RNA, DNA, and intact virions can be encapsulated within the aqueous interior and be delivered to cells in a biologically active form (Fraley, et al., Trends Biochem. Sci., (1981) 6:77). In order for a liposome to be an efficient gene transfer vector, one or more of the following characteristics should be present: (1) encapsulation of the gene of interest at high efficiency with retention of biological activity; (2) delivery of the aqueous contents of the vesicle to the target cell cytoplasm at high efficiency; and (3) accurate and effective expression of genetic information.

Liposomes are commercially available from Gibco BRL, for example, as LIPOFECTIN™ and LIPOFECTACE™, which are formed of cationic lipids such as N-[1-(2,3dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, (1985) 3:235–241.

Compaction agents also can be used alone, or in combination with, a biological or chemical/physical vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the ica molecule in a form that is more efficiently taken up by the cell or, more preferably, in combination with one or more of the above-described vectors.

Other exemplary compositions that can be used to facilitate uptake by a target cell of the ica nucleic acids include calcium phosphate and other chemical mediators of intracellular transport, microinjection compositions, electroporation and homologous recombination compositions (e.g., for integrating a ica nucleic acid into a preselected location within the target cell chromosome).

EXAMPLES

Example 1

Purification of PS/A Antigen.

It has been discovered according to the invention that PS/A can be purified from any bacterial strain expressing the ica locus. Specifically, these include *Staphylococcus epidermidis, Staphylococcus aureus*, and other *Staphylococcal* strains such as *Staphylococcus carnosus* transformed with the genes in the ica locus. The following specific strains have been used according to the invention to purify PS/A from include *S. epidermidis* RP62A (ATCC Number: 35984), *S. epidermidis* RP12 (ATCC Number: 35983), *Staphylococcus epidermidis* M187, *S. carnosus* TM300 (pCN27), *S. aureus* RN4220 (pCN27), and *S. aureus* MN8 mucoid.

1. Method of purification of PS/A from coagulase-negative *staphylococci* containing the ica locus that encodes production of proteins needed to synthesize PS/A:

Starting material was prepared from cultures of *staphylococci* expressing the ica genes by growing the bacteria in any growth medium supporting the growth of these *staphylococcal* strains. A preferred medium is a chemically defined medium (CDM) (Hussain, M., J. G. M. Hastings and P. J. White. 1991. A chemically defined medium for slime production by coagulate-negative *Staphylococci*. *J. Med. Microbiol*. 34:143) composed of RPMI-1640 AUTO-MOD, an RPMI-1640 preparation modified to allow sterilization by autoclaving; (Sigma Chemical Co., St. Louis, Mo.) as a starting base. Phenol red was omitted because it readily binds to purified PS/A. The CDM is supplemented with additional amino acids, vitamins, and nucleotides to give it a final composition similar to that described elsewhere (Hussain, M., J. G. M. Hastings and P. J. White. 1991. A chemically defined medium for slime production by coagulate-negative *Staphylococci*. *J. Med. Microbiol*. 34:143). The medium was further supplemented with dextrose and sucrose; each was autoclaved separately and then added to a final concentration of 1%.

Cultures were inoculated with a single colony of *staphylococci* (Muller, E., J. Huebner, N. Gutierrez, S. Takeda, D. A. Goldmann and G. B. Pier. 1993. Isolation and characterization of transposon mutants of *Staphylococcus epidermidis* deficient in capsular polysaccharide/adhesin and slime. *Infect Immun*. 61:551) from an agar plate such as trypticase soy agar, that had been incubated overnight at 37° C. Cultures were grown with vigorous mixing at 37° C., with 2 L of $O_2$/min bubbled through via a sparger and the pH maintained at 7.0 by automatic addition of 5 M NaOH with a pH titrator. Cultures were grown until they ceased to need addition of NaOH to maintain the pH at 7.0 (i.e., for 48–72 hours).

Crude antigen was extracted from the bacterial cells directly into the culture supernatant with use of divalent cations, low pH, and heat. A preferred method is to add $MgCl_2$ to the culture to a final concentration of 100 mM, and to adjust the pH to 5.0. The culture was then heated and stirred. A temperature of 65° C. for 90 min was satisfactory. The cell bodies were sedimented at 9000×g for 15 min. The supernatant was concentrated to ~1000 ml via tangential-flow filtration (10,000 molecular weight (MW) cutoff filter), and the following buffer exchanges and treatments were performed while the solution was still in the filtration device: The buffer was exchanged with deionized $H_2O$ adjusted to a pH of 5.0 (to remove excesses of $Mg^{2+}$ ions). Next the pH was adjusted to 7.4 with 0.1 M TRIS-0.15 M NaCl, and the solution was treated for 4 hours at room temperature with 5 mg each of RNase and DNase and then for 2 hours with 5 mg of trypsin. The buffer was changed in the tangential flow device to 10 mM EDTA (pH 8.6), and sodium deoxycholate (DOC) added to a final concentration of 3%.

Another preferred method for isolating the polysaccharide antigen of the invention involves incubating the bacteria with a strong base or acid, such as 5 Molar NaOH or HCL. The bacteria are stirred in the strong base or acid for 18–24 hours. The cell bodies are then collected by centrifugation and re-extracted two more times. The supernatant from each of the extractions is pooled and neutralized to pH 7 using an acid or base. The resulting crude antigen suspension is dialized against deionized water for 2–24 hours. The remaining insoluble crude antigen is collected by centrifugation. The supernatant is tested for the presence of soluble antigen by known assays, such as immunological means. If the supernatant is positive for soluble antigen, the supernatant can be lyophilized and re-extracted to obtain additional crude antigen. The insoluble crude antigen is resuspended in a buffer solution of 50 mM PBS or 100 mM Tris with 150 mM NaCl.

The suspended crude antigen was treated with 5 mg each of RNase and DNase for 4 hours at 37° C. and then with 5 mg of trypsin for 2 hours; the cells were sedimented, and this supernatant added to the concentrated culture supernatant as it was being treated with trypsin. The remaining cell bodies were resuspended in 10 mM EDTA/3% DOC (pH 8.6); stirred for 2 hours and sedimented a third time. The resultant supernatant was added to the concentrated culture supernatant as it was being treated with 10 mM EDTA/3% DOC (pH 8.6). Another alternative is a buffer with a pH>10. A preferred buffer is 0.4 M ammonium carbonate at a pH of 11. Finally, the pooled supernatants were concentrated via stirred-cell filtration using, for example, a 30,000 MW cutoff membrane filter). Particulate or insoluble material was sedimented by centrifugation at 2,000×g for 30 min and the supernatant retained.

As an alternative to using the above extractions and DOC buffers to obtain dissolved, crude antigen, crude antigen was also obtained from the initial extracts of the cells by adjusting the pH of the extracts to >8.0 with base such as sodium hydroxide, adding 4 volumes of alcohol such as ethanol, recovery of the precipitated material by centrifugation, and redissolution of the precipitate in 0.1 M HCL or any buffer with a pH below 4.0.

High-molecular-weight PS/A-enriched material was next isolated from the crude slime extract by molecular sieve chromatography. A 5.0-cm×100-cm column was packed with SEPHAROSE CL-4B™ (Pharmacia, Piscataway, N.J.) or a comparable molecular sieve gel and washed with 10 mM EDTA containing 1% DOC (pH 8.6). As an alternative a buffer with a pH<4.0 was sometimes used. A preferred buffer was 0.1 m glycine-HCL at a pH of 2.0. Crude slime is applied in a volume of 10–20 ml and the PS/A containing fractions were identified by measurement of the absorption of UV light at 206 nm and immuno-dot-blot analysis using a polyclonal rabbit antiserum specific to the PS/A antigen.

Material eluting in the void-volume fractions (MW>100,000 Daltons) of columns using DOC-based buffers was pooled and treated with proteinase K (0.1 mg/ml), which is proteolytically active in 1% DOC; the material was simultaneously concentrated to 100 ml with a stirred-cell filtration unit (30,000 MW cutoff membrane). Material eluting in the void volume of a molecular sieve column with a low pH buffer (<4.0) was pooled, sodium phosphate dibasic added to a final concentration of at least 0.1 M and a pH of at least 8.0, and then 4 volumes of alcohol, such as 95% ethanol, was added to precipitate the PS/A antigen.

Further purification of material recovered from DOC columns used a step to destroy remnants of an alkali-labile cell wall antigen present in the preparations. The proteinase K-digested material was treated by the addition of NaOH to a final concentration of 500 mM and the mixture was stirred at 22° C. for 2 hours and then neutralized with HCL. PS/A was recovered by alcohol precipitation (such as methanol added to 50% v/v) and sedimented by centrifugation at 30,000×g for 30 min. Residual DOC and impurities were removed by numerous washes of the precipitate with pure methanol.

To remove residual teichoic acid from material recovered in the void volume of columns run using either the DOC-buffer system or low pH buffer system, the alcohol precipitates were suspended in 24% (v/v) hydrofluoric acid (HF) at 4° C. for 48 hours. The HF solution was diluted in water to a concentration of 12% HF, then neutralized with NaOH and dialyzed against running water. PS/A was mostly insoluble at this point. Any remaining soluble PS/A was precipitated by the addition of methanol to 50%, the pellet was washed with pure methanol 3 to 5 times, suspended in deionized $H_2O$, frozen, and lyophilized.

2. Purification of PS/A from *Staphylococcus aureus*.

PS/A was also purified from *S. aureus* using either the above procedure for coagulate-negative *staphylococci* or a modification of the above procedure. The recovery of PS/A from *S. aureus* preferably was facilitated by using a strain that constitutively makes PS/A such as the MN8 mucoid strain. Such strains can be grown in any medium that supports their growth although a preferred medium is columbia broth. Alternately, any *S. aureus* strain with an intact ica locus can be grown in brain heart infusion broth supplemented with glucose at Æ0.25% (v/v) to produce PS/A.

Cultures were inoculated with a single colony of *Staphylococcus aureus* from any appropriate medium that had been incubated overnight at 37° C. Cultures were grown with vigorous mixing at 37° C., with 2 L of $O_2$/min bubbled through via a sparger and the pH maintained at 7.0 by automatic addition of 5 M NaOH with a pH titrator. Cultures were routinely grown until they cease to need addition of NaOH to maintain the pH at 7.0 (i.e., for 48–72 hours).

The bacterial cells were then recovered from the culture by centrifugation and resuspended in buffered saline. Then lysozyme and lysostaphin enzymes were added in concentrations of >0.1 mg/ml. This suspension was stirred for 2–24 hours at 37° C., after which a protease was added. A preferred protease was Proteinase K at a concentration of at least 0.1 mg/ml, although other proteases such as Pronase E or trypsin can be used. The mixture was stirred at 37° C. for at least 2 hours. The pH of the suspension was then lowered to below 4.0, but preferably to below 2.0, using acid such as HCL. The insoluble material was removed by centrifugation and the precipitate re-extracted 3 times by resuspension in low pH (<4.0, preferably <2.0) solutions followed by stirring for Æ10 minutes and centrifugation to remove insoluble materials. The low-pH extracts were pooled, the pH raised to above 8.0 by addition of both sodium phosphate to a concentration of Æ0.1 M and a base such as sodium hydroxide, and then 4 volumes of alcohol such as 95% ethanol were added. Another alternative is a buffer with a pH>10. A preferred buffer is 0.4 M ammonium carbonate at a pH of 11.

Another preferred method for isolating the polysaccharide antigen of the invention involves incubating the bacteria with a strong base or acid, such as 5 M NaOH or HCL. The bacteria are stirred in the strong base or acid for 18–24 hours. The cell bodies are then collected by centrifugation and re-extracted two more times. The supernatant from each of the extractions is pooled and neutralized to pH 7 using an acid or base. The resulting crude antigen suspension is dialyzed against deionized water for 2–24 hours. The remaining insoluble crude antigen is collected by centrifugation. The supernatant is tested for the presence of soluble antigen by known assays, such as immunological means. If the supernatant is positive for soluble antigen, the supernatant can be lyophilized and re-extracted to obtain additional crude antigen. The insoluble crude antigen is resuspended in a buffer solution of 50 mM PBS or 100 mM Tris with 150 mM NaCl. The material was then subjected to the same enzymatic treatments as described above with respect to purification method of PS/A from coagulase-negative *staphylococci*.

Another preferred method for isolating the polysaccharide antigen of the invention involves recovering the cell-free supernate of the bacterial culture and isolating the material from this solution, One means to isolate the polysaccharide is to concentrate the supernate using membranes that retain molecules of >100,000, although any membrane with an ability to retain molecules in the range of 500–2,000,000 Daltons could be used. Once concentrated a solvent such as methanol, ethanol, acetone or other material capable or causing the polysaccharide to become insoluble is added in a sufficient volume to precipitate the polysaccharide. Alternately the solvent can be added directly to the unconcentrated culture supernate. The insoluble, precipitated polysaccharide is collected and resuspended in a buffer solution. The material was then subjected to the same enzymatic treatments as described above with respect to purification method of PS/A from coagulase-negative *staphylococci*.

The insoluble material was then recovered by centrifugation, redissolved in low pH (<4.0, preferably 1.0) solutions, insoluble material was removed by centrifugation, and the high molecular weight material in the soluble fraction recovered by application to a molecular sieve column equilibrated in a buffer below pH 4.0. The preferred buffer was 0.1 M glycine-HCL at a pH of 2.0. A typical molecular sieve column has dimensions of 2.6×100 cm and was packed with a gel such as SEPHACRYL S-500™ (Pharmacia). The PS/A containing fractions were identified by measurement of the absorption at 206 nm and immuno-dot-blot analysis with polyclonal rabbit antiserum to PS/A. Immunologically reactive fractions eluting in the high molecular (>100,000) weight range were pooled, the pH raised to >8 by addition of both sodium phosphate to a concentration of Æ0.1 M and a base (such as sodium hydroxide) followed by addition of 4 volumes of an alcohol such as ethanol and the resultant precipitate recovered by centrifugation. The alcohol precipitates were next suspended in 24% (v/v) hydrofluoric acid (HF) at 4° C. for 48 hours. The HF solution was diluted in water to a concentration of 12% HF, then neutralized with NaOH and dialyzed against running water. PS/A was mostly insoluble at this point. Any remaining soluble PS/A was precipitated by the addition of alcohol to >50% final concentration, the pellet was washed with alcohol such as 95% ethanol or pure methanol 3 to 5 times, and the pellet was suspended in deionized $H_2O$, frozen, and lyophilized.

Example 2

Analysis of the PS/A Antigen.

Use of both base (NaOH) and hydrofluoric acid treatments to degrade contaminants significantly improve the purity of PS/A over prior art preparations previously obtained. PS/A eluted in the high molecular weight, void-volume fractions of a SEPHAROSE 4B™ column (>100,000 kDa) and gave a single precipitin band in immunodiffusion, as previously shown (Tojo, M., N. Yamashita, D. A. Goldmann and G. B. Pier. 1988. Isolation and characterization of a capsular polysaccharide/adhesin from *Staphylococcus epidermidis*. *J Infect Dis*. 157:713). In addition, sensitization of ELISA wells with dilutions of PS/A down to 0.02 μg/well resulted in the binding of significantly more of a 1:500 dilution of antibody to purified PS/A than of preimmune serum. Use of 3% DOC or low pH buffers (<4.0) to solubilize PS/A during purification was found to be important, but once the PS/A was precipitated from these solutions by methanol, it could not be resolubilized at a pH of >4.0, even in DOC buffers. PS/A was slightly soluble (~500 μg/ml) in 50% propanol-50% butanol and in pyridine. The PS/A antigen was devoid of detectable phosphate (<0.01%) (Keleti, G. and W. H. Lederer. 1974. Handbook of Micromethods for the Biological Sciences. Van Nostrand Reinhold Co., New York).

Example 3

Analysis of the Chemical Properties of PS/A.

When we analyzed PS/A isolated from *S. epidermidis* M187, *S. carnosus* (pCN27) and *S. aureus* MN8 mucoid after dissolution in 4M DCI acid at room temperature, we found that glucosamine was the single sugar component in PS/A using and nuclear magnetic resonance (NMR). Acetate was also detected at a ~1:1 molar ratio to glucosamine. A representative NMR spectrum is shown in FIG. 1. Hydrolysis of PS/A into oligosaccharide fragments by ozone and analysis by NMR established the linkage between the sugars as a beta linkage. PS/A isolated from these strains loses serologic reactivity and chemical properties detectable by GLC-MS after treatment with sodium periodate (0.2 M for 14 h), indicating a 1–6 linkage between the glucosamine residues. Also, hydrolysis with 5 M NaOH for >5 min destroys serologic activity.

Thus the native PS/A material is a high molecular weight (>100,000 Daltons) homopolymer of N-acetyl D-glucosamine residues linked to each other in a beta 1–6 linkage. The level of substitution of the acetate groups on the amino group of the glucosamine approaches 100% in some preparations of the native molecule.

Example 4

Immunization with Purified PS/A Elicits Antibodies Reactive with the Antigen.

Method: Previously described methods for eliciting antibodies to PS/A by immunization of rabbits (Kojima, Y., M. Tojo, D. A. Goldmann, T. D. Tosteson and G. B. Pier. 1990. Antibody to the capsular polysaccharide/adhesin protects rabbits against catheter related bacteremia due to coagulase-negative *staphylococci*. *J Infect Dis*. 162:435; Tojo, M., N. Yamashita, D. A. Goldmann and G. B. Pier. 1988. Isolation and characterization of a capsular polysaccharide/adhesin from *Staphylococcus epidermidis*. *J Infect Dis*. 157:713; Takeda, S., G. B. Pier, Y. Kojima, M. Tojo, E. Muller, T. Tosteson and D. A. Goldmann. 1991. Protection against endocarditis due to *Staphylococcus epidermidis* by immunization with capsular polysaccharide/adhesin. *Circulation*. 84:2539) were used to prepare antisera from the antigen isolated from *S. epidermidis* M187 and *S. aureus* MN8 mucoid.

Results: The antibodies elicited by preparations from both bacterial strains induced antibodies of comparable titers to both antigens (Table 1).

TABLE I

Binding of antibodies raised to MN8-mucoid and *S. epidermidis* PS/A to each others antigen in ELISA

| ELISA for MN8-mucoid coated PS/A plates (2 g/well) | |
| --- | --- |
| Anti-sera diluted 1:500 | $O.D_{405\ nm}$ |
| anti-MN8 mucoid PS/A | 0.856 |
| anti-*S. epidermidis* PS/A | 0.872 |
| Normal rabbit sera | 0.000 |
| ELISA for *S. epidermidis* coated PS/A plates (2 g/well) | |
| Anti-sera diluted 1:500 | $O.D_{405\ nm}$ |
| anti-MN8 mucoid PS/A | 0.770 |
| anti-*S. epidermidis* PS/A | 0.886 |
| Normal rabbit sera | 0.013 |

Example 5

Physical Location of PS/A Antigen on *Staphylococcal* Strains.

Methods: *S. aureus* strains MN8 mucoid and RN4220 (pCN27) were grown on trypticase soy agar, and *S. aureus* MN8 was grown in Brain Heart Infusion Broth supplemented with Æ0.25% glucose. The cells were then probed first with polyclonal rabbit antiserum to PS/A and then with gold-labeled protein A, or gold-labeled antirabbit IgG, and micrographs were obtained.

PS/A has been previously shown to represent the bacterial capsule for *S. epidermidis*. We investigated whether strains carrying the ica locus were encapsulated using immunoelectron microscopy. A series of immunoelectron microscopic photographs of: (a) interaction of anti-PS/A antibodies with a PS/A capsule on *S. aureus* strain MN8 mucoid; (b) negative control using normal rabbit serum (NRS) staining of *S. aureus* strain MN8 mucoid; (c) interaction of anti-PS/A antibodies with PS/A capsule on *S. aureus* strain RN4220 (pCN27); (d) negative control using NRS staining of *S. aureus* strain RN4220; (e) interaction of anti-PS/A antibodies with *S. aureus* strain MN8 grown in brain heart infusion broth supplemented with 0.25% glucose; and (f) negative control using NRS staining of *S. aureus* strain MN8 grown in brain heart infusion broth supplemented with 0.25% glucose were taken. The micrographs demonstrate that antibodies to PS/A bind to an extracellular capsule in these strains.

Example 6

Expression of PS/A Antigen by Human Clinical Isolates of *S. aureus*.

Figure 2:
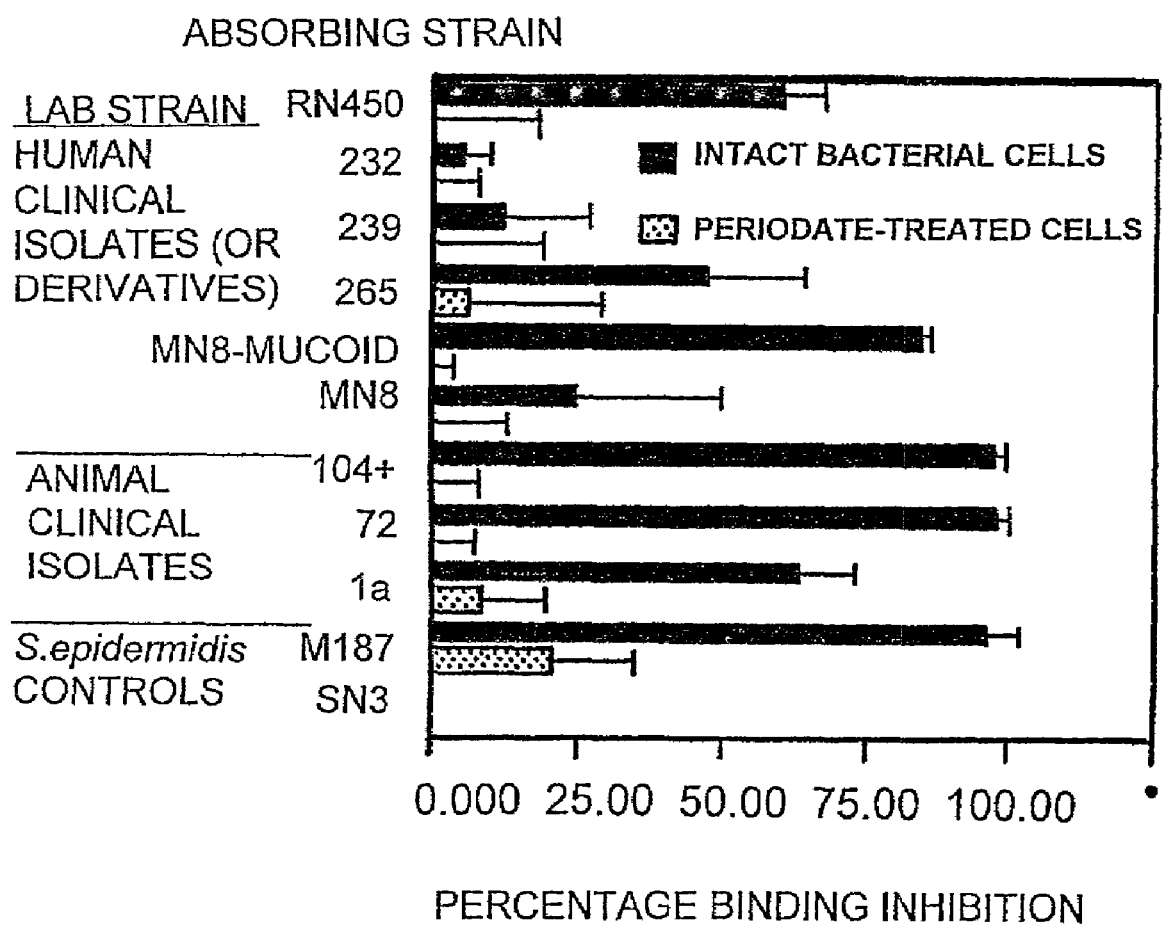
FIG. 2 is a graph depicting the results of an ELISA inhibition showing the ability of various strains of *Staphylococcus aureus* grown overnight two times in brain heart infusion broth supplemented with 0.5% glucose to remove antibodies binding to PS/A antigen that has sensitized the ELISA plate (speckled bars). As a control for specificity a separate aliquot of the same bacteria was treated with 0.4 M sodium metaperiodate to destroy the PS/A antigen on the surface of the *S. aureus* strains (gray bars). The percentage inhibition of binding was determined from the ratio of the optical density achieved using antibody to PS/A adsorbed with the test strain and antibody to PS/A adsorbed with a known PS/A negative strain (*S. epidermidis* sn-3).

Many human clinical isolates of *S. epidermidis* express PS/A antigens constitutively (i.e., all of the time under a variety of growth conditions). Also, some strains of *S. aureus* do the same (i.e., MN8 mucoid). However most human clinical isolates of *S. aureus* do not express much PS/A when grown under normal laboratory conditions. We found that if these *S. aureus* strains were grown in brain heart infusion broth medium containing Æ0.25% glucose, then expression of PS/A could be detected by serologic means such as an ELISA inhibition assay (shown in FIG. 2). In addition, we found that isolates of *S. aureus* that do not express detectable PS/A prior to infection of mice can be shown to produce PS/A when recovered from an infected tissue such as the kidney. Thus under specialized in vitro conditions or following experimental infections in animals, strains of *S. aureus* that otherwise do not make detectable PS/A now do so. Another medium, we have found to enhance PS/A expression in vitro is *Staphylococcus* 110 medium.

An immunoelectron microscopy photograph of a human clinical isolate (ASEAN) freshly isolated from agar to detect PS/A expression and stained with (a) anti-PS/A antibodies, or (b) NRS control was taken. We found that human clinical isolates of *S. aureus* express PS/A when strains were tested by transmission electron microscopy from an agar plate that was first used to detect infection in a sample of fluid or tissue. Thus if human clinical isolates were tested for PS/A expression without extensive passage of the bacteria on laboratory media then it can be shown that they make PS/A antigen.

Example 7

Expression of PS/A Antigen by Animal Isolates of S. aureus.

S. aureus is the major cause of mastitis infections in animals and causes considerable economic losses. We have also analyzed S. aureus isolates from animals (cows and sheep) for the expression of PS/A. We have found many of the isolates analyzed make the PS/A antigen, as determined by serologic testing. Out of 40 animal isolates tested, 23 had strong reactions in immuno-dot blots with antibodies to PS/A. This was detectable even though the isolates were not grown in special media to enhance production of PS/A as must be done with human isolates. Thus, unlike human clinical isolates of S. aureus, many animal isolates seem to be capable of making the PS/A constitutively.

Example 8

Protection Against S. aureus Infection by Antibodies to PS/A.

Methods: PS/A antigen 1–100 µg (preferred 100 µg/mouse) was used to immunize mice to elicit antibodies. The mice were then challenged with live S. aureus bacteria, either S. aureus strain Reynolds or strain MN8 and those with antibodies to PS/A were shown to be protected against infection.

Figure 3:
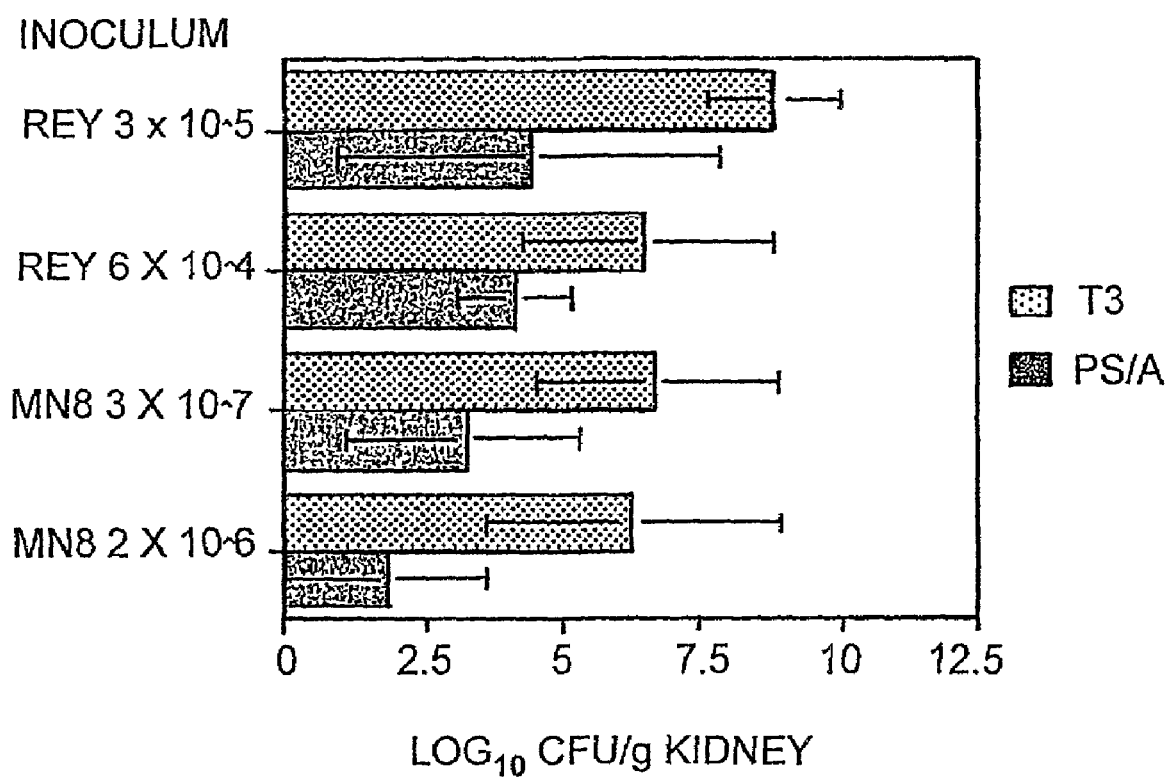
FIG. 3 is a graph depicting the ability of a PS/A antigen to induce active immunity in mice against *S. aureus* infection.

Results: Actively immunizing mice with PS/A followed by intravenous challenge with S. aureus reduced the number of bacteria in the kidney's five days later when the animals were killed and tested (FIG. 3).

Figure 4:
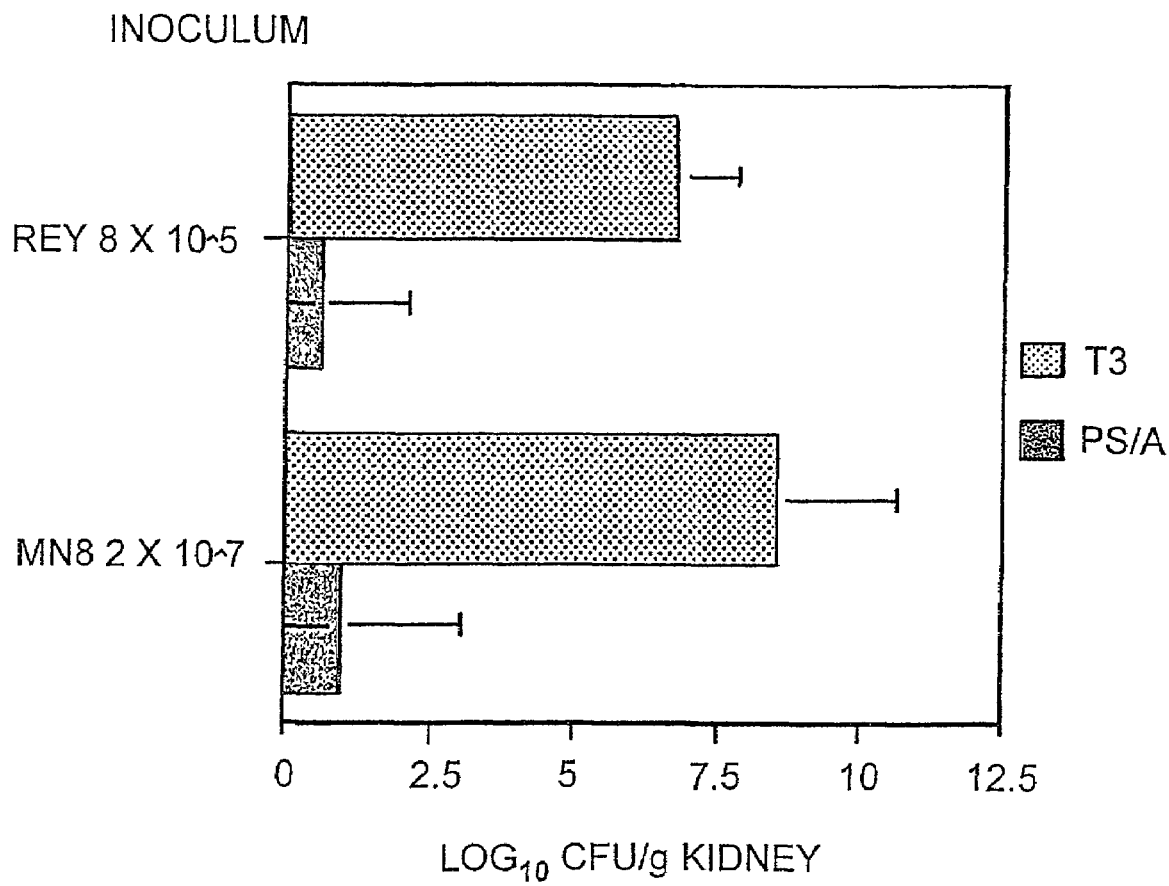
FIG. 4 is a graph depicting the ability of an anti-PS/A antibody to induce passive immunity in mice against *S. aureus* infection.

Similarly, giving mice antibodies raised in rabbits to the PS/A antigen followed by challenge of the mice with S. aureus strains protects the mice against S. aureus infection (FIG. 4). Thus antibodies to PS/A protect mice against S. aureus infection. As noted above, analysis of the isolates recovered from the infected kidneys of nonimmune control mice showed that infection had induced expression of PS/A during the time of infection in the animal.

Example 9

Detection of Genes for PS/A Production in Isolates of S. aureus.

Methods: DNA extraction from bacteria, PCR analysis and Southern blot analysis:

DNA preparation: Bacteria were inoculated in 10–2-ml of trypticase soy broth (TXB) and grown overnight at 37° C. The resulting growth was recovered by centrifugation. The bacterial cells were resuspended in lysis buffer (25 mM Tris, pH 8.0, 25 mM EDTA, 300 mM sucrose). Cells were then incubated with lysostaphin (0.2 mg/ml) and lysozyme (2 mg/ml) for 1–3 hours at 37° C. Following this enzyme digestion, 0.5 ml of 5% sodium dodecyl sulfate (SDS) in 45% ethanol was added, vortexed and incubated for 30 min at room temperature. One ml of buffered phenol/chloroform/isoamyl alcohol (volume ratios of 27:12:1) was then added followed by vortexing and centrifugation (15 min, 5000 rpm, 4° C.). The upper aqueous layer was removed and added to chloroform:Isoamyl alcohol (24:1 ratio). Again this was centrifuged (15 min, 5000 rpm, 4° C.). the DNA was recovered in the upper aqueous layer, then precipitated by addition of 95% ethanol to amount equal to double the starting volume, and the precipitated DNA spooled onto a glass rod. The DNA was then dissolved in distilled water.

Restriction enzyme digestion of DNA for Southern blot analysis was done according to the manufacturer's protocol (Gibco BRL, Grand Island, N.Y.). The DNA probe was labeled using the ECL protocol (Amersham International plc, Buckinghamshire, England) following the manufacturer's instructions.

PCR was performed using a touch down protocol. Briefly, primers (SEQ. ID. NO. 2–3) were added to the DNA obtained from the Staphylococcal strains (200 nM final concentration) and the thermal cycler programmed to perform DNA melting at 95° C. and polymerase extensions starting at 60° C. with decreasing annealing temperatures of 0.5° C. used at each cycle until reaching 45° C.

Results: Using the polymerase chain reaction (PCR) we have shown that isolates of S. aureus have the genes to make PS/A. These genes are contained in a locus designated ica and were originally isolated and sequenced by Heilmann et al. (Heilmann, C., O. Schweitzer, C. Gerke, N. Vanittanakom, D. Mack and F. Gotz. 1996. Molecular basis of intercellular adhesion in the biofilm-forming Staphylococcus epidermidis. Molec. Microbiol. 20:1083). We demonstrate herein that the ica locus encodes proteins that synthesize the high molecular weight PS/A molecules as well as the poly-N-acetylated polyglucosamine molecule termed PIA.

Figure 5:
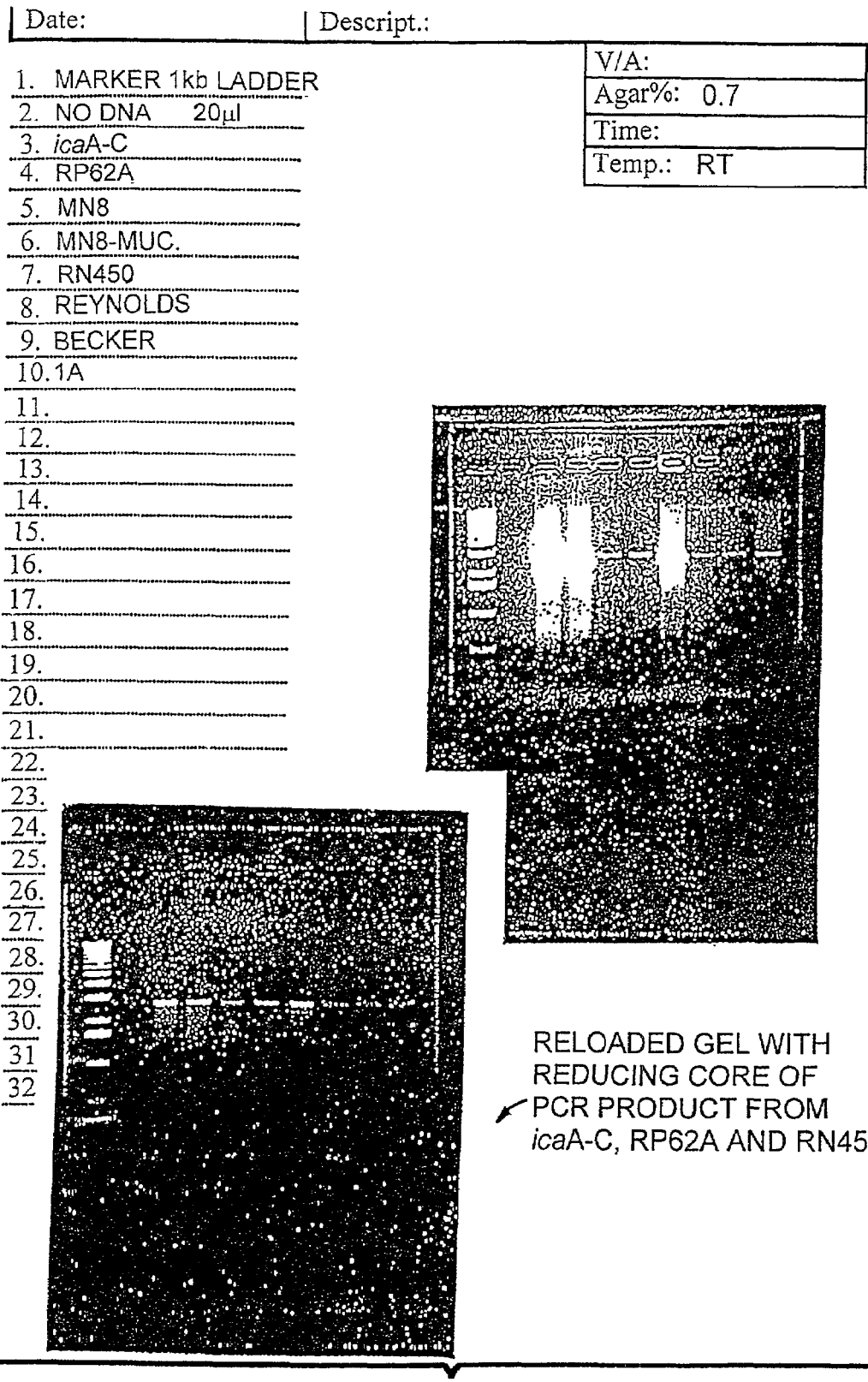
FIG. 5 shows a photograph of a PCR fragment gel.
Figure 6:
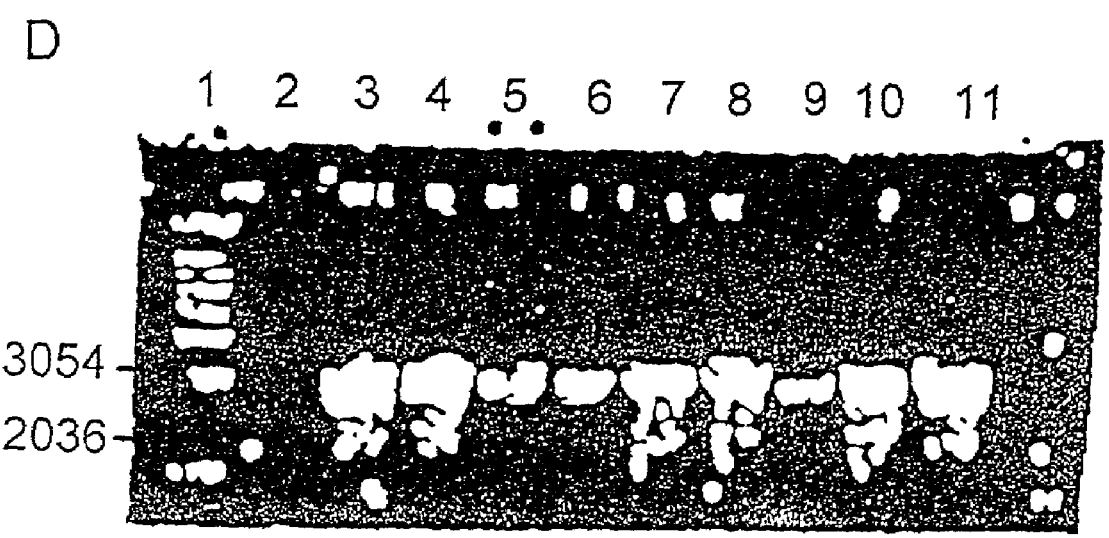
FIG. 6 shows a photograph of a Southern blot of ica (intercellular adhesin locus) genes in *S. aureus*. PCR was performed on chromosomal DNA from controls and eight isolates of *S. Aureus*: (1) molecular weight markers (2) *S. Carnosus* TM300, negative control (3) positive control DNA from *S. Epidermis* RP62A *staphylococcus aureus* strains (4) Reynolds (5) MN8 (6) 5827 (7) S836 (8) Vas (9) VP (10) 265 (11).

Primers were designed for the PCR analysis based on the sequence of the ica genes to amplify a fragment of DNA of 2.7 kB (SEQ ID No: 2 and 3). When these primers were mixed with DNA isolated from S. aureus strains MN8, MN8 mucoid, RN450, Becker, Reynolds and 1A, along with DNA from S. epidermidis strain RP62A, from which the ica genes had originally been cloned, and used in a PCR reaction we found that all of the S. aureus strains had the ica locus (FIG. 5). When the amplified 2.7 kB fragment was labeled and used as a probe in a Southern blot reaction of DNA extracted from these S. aureus strains, we also detected the presence of the genes in the ica locus (FIG. 6). We have thus shown that the genes needed to make to proteins to synthesize the PS/A antigen are present in S. aureus.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. An isolated pure *staphylococcal* capsular polysaccharide/adhesin antigen (PS/A) having a molecular weight of greater than 100,000 daltons wherein the *staphylococcal* PS/A is prepared according to a process comprising:

preparing an impure PS/A from a *staphylococcal* culture;
incubating the impure PS/A from said *staphylococcal* culture with a strong base or a strong acid to produce a semi-pure PS/A preparation;
neutralizing the semi-pure PS/A preparation with an acid or base;
precipitating the neutralized semi-pure PS/A preparation with an alcohol followed by molecular sieve chromatography and digestion with a proteinase;
incubation of the proteinase-digested PS/A preparation with a base followed by neutralization with an acid;
incubation of the neutralized proteinase-digested PS/A preparation with hydrofluoric acid followed by neutralization with NaOH and precipitation with an alcohol to produce the isolated pure PS/A, wherein the isolated pure PS/A is greater than 92% free of contaminants and contains less than 10% galactose.

2. The isolated pure PS/A of claim 1, wherein the PS/A has glucosamine residues and wherein at least 50% of the glucosamine residues are substituted with acetate.

3. The isolated pure PS/A of claim 1, wherein the PS/A has glucosamine residues and wherein at least 50% and 95% of the glucosamine residues are substituted with acetate.

4. The isolated pure PS/A of claim 1, wherein the impure PS/A is incubated with said strong acid and neutralized with said base.

5. The isolated pure PS/A of claim 1, wherein the isolated pure PS/A is further precipitated with an alcohol.

6. The isolated pure PS/A of claim 5, wherein the alcohol is methanol or ethanol.

7. The isolated pure PS/A of claim 1, wherein the PS/A has less than 5% galactose.

8. The isolated pure PS/A of claim 1, wherein the PS/A has less than 1% galactose.

9. A pharmaceutical composition comprising the isolated pure PS/A of claim 1, and a pharmaceutically-acceptable carrier.

10. A pharmaceutical composition comprising the isolated pure PS/A of claim 2, and a pharmaceutically-acceptable carrier.

11. A pharmaceutical composition comprising the isolated pure PS/A of claim 3, and a pharmaceutically-acceptable carrier.

* * * * *